(12) United States Patent
Sharma et al.

(10) Patent No.: US 11,969,173 B2
(45) Date of Patent: Apr. 30, 2024

(54) REPOSITIONABLE OVER THE SCOPE CLIP

(71) Applicants: BOSTON SCIENTIFIC MEDICAL DEVICE LIMITED, Galway (IE); BOSTON SCIENTIFIC SCIMED, INC., Maple Grove, MN (US)

(72) Inventors: Deepak Kumar Sharma, Muzaffarnagar (IN); Paul Smith, Smithfield, RI (US); Sharath Kumar G, Kanakapura (IN); Rajivkumar Singh, Thane (IN); Arun Adhikarath Balan, Aluva (IN)

(73) Assignees: BOSTON SCIENTIFIC MEDICAL DEVICE LIMITED, Galway (IE); BOSTON SCIENTIFIC SCIMED, INC., Maple Grove (IE)

( * ) Notice: Subject to any disclaimer, the term of this patent is extended or adjusted under 35 U.S.C. 154(b) by 25 days.

(21) Appl. No.: 17/660,772

(22) Filed: Apr. 26, 2022

(65) Prior Publication Data

US 2022/0378432 A1 Dec. 1, 2022

Related U.S. Application Data

(60) Provisional application No. 63/202,085, filed on May 26, 2021.

(51) Int. Cl.
*A61B 1/00* (2006.01)
*A61B 17/122* (2006.01)
*A61B 17/128* (2006.01)

(52) U.S. Cl.
CPC ...... *A61B 17/1227* (2013.01); *A61B 1/00135* (2013.01); *A61B 1/0014* (2013.01); *A61B 17/1285* (2013.01); *A61B 2217/005* (2013.01)

(58) Field of Classification Search
CPC ............ A61B 17/1227; A61B 17/1285; A61B 1/0014; A61B 1/00135; A61B 17/083;
(Continued)

(56) References Cited

U.S. PATENT DOCUMENTS

| 6,074,408 A | * | 6/2000 | Freeman | ............... A61B 17/29 606/205 |
| 2004/0006256 A1 | | 1/2004 | Suzuki et al. | |

(Continued)

FOREIGN PATENT DOCUMENTS

| CN | 111 214 271 | 6/2020 | |
| WO | WO-2019135958 A2 | * 7/2019 | ........... A61B 17/083 |

*Primary Examiner* — Erich G Herbermann
*Assistant Examiner* — Aman Kumar Mann
(74) *Attorney, Agent, or Firm* — Fay Kaplun & Marcin, LLP

(57) ABSTRACT

A clipping system includes an adapter configured to be mounted over an insertion device and a clip including first and second jaws movable between an insertion configuration and an initial deployed configuration. A first extending member is releasably coupled to the clip and movably connected to the adapter to permit a movement of the clip relative to the adapter from the insertion configuration to the initial deployed configuration. The first extending member is configured to permit withdrawal of the adapter away from the clip to place the system in a review configuration to enhance a visual observation of the clip. The first extending member is operable to retract the clip over the adapter so that the clip is forced open, freeing the clip from tissue on which it has been clipped. The first extending member is configured to release the clip therefrom in a final deployed configuration.

15 Claims, 14 Drawing Sheets

(58) Field of Classification Search
CPC .......... A61B 17/10; A61B 2017/00296; A61B 1/00087; A61B 17/122; A61B 2017/00818; A61B 17/12013; A61B 2017/12018; A61B 17/068
See application file for complete search history.

(56) References Cited

U.S. PATENT DOCUMENTS

| | | | |
|---|---|---|---|
| 2014/0228864 A1* | 8/2014 | Jugenheimer | A61B 17/122 606/157 |
| 2020/0397445 A1 | 12/2020 | Shikhman et al. | |
| 2021/0045747 A1* | 2/2021 | Zhong | A61B 17/064 |
| 2023/0181194 A1* | 6/2023 | Braun | A61B 17/1285 606/142 |

* cited by examiner

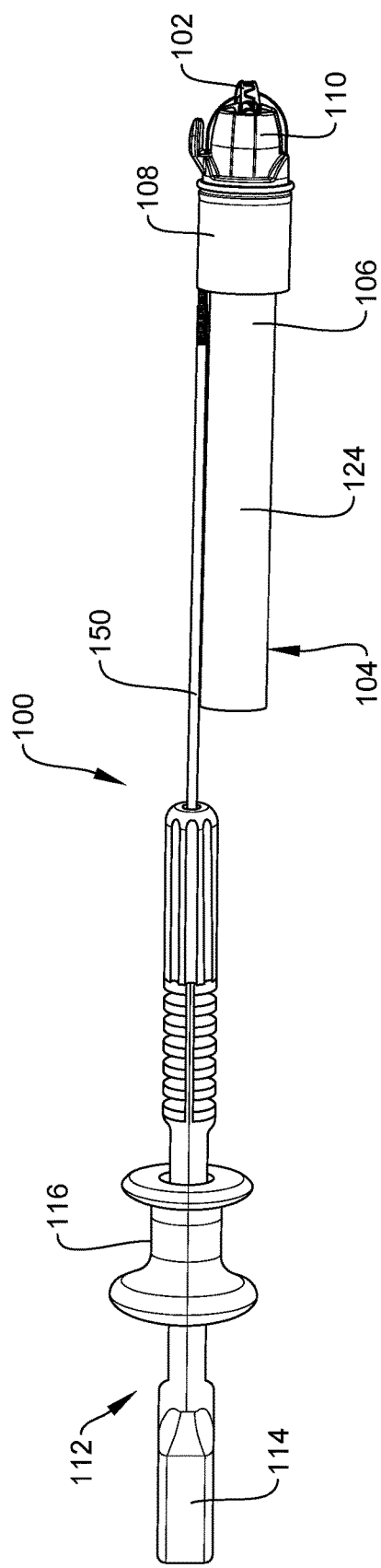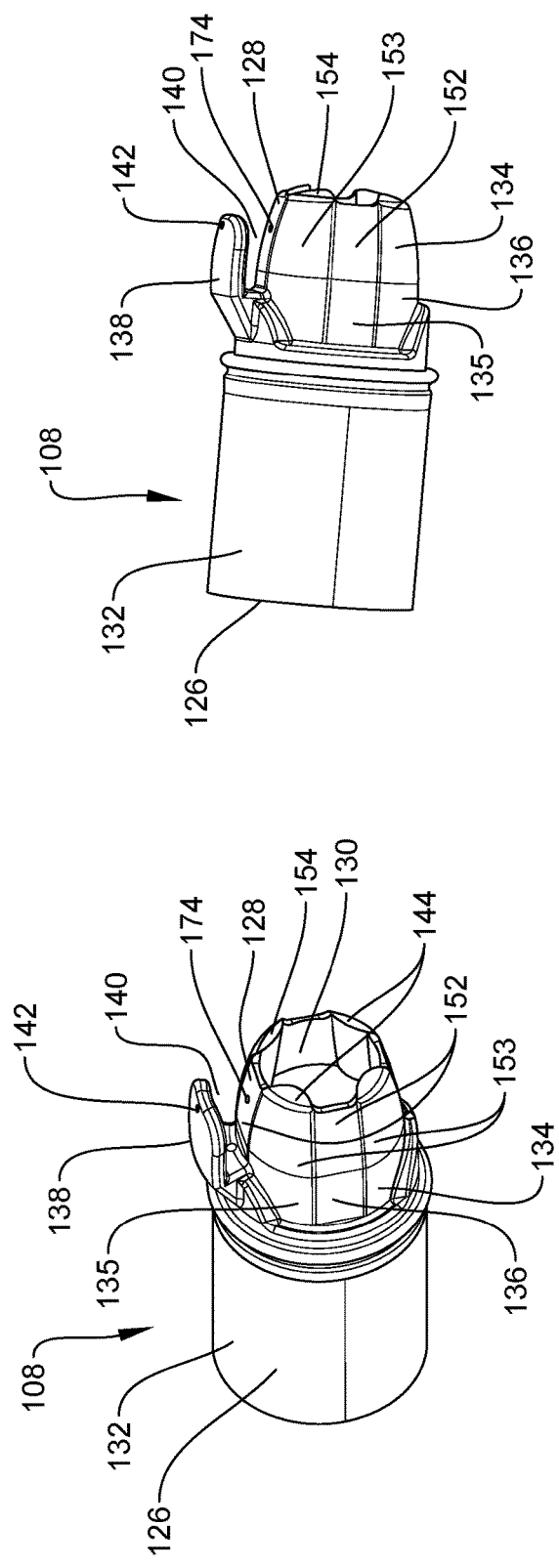

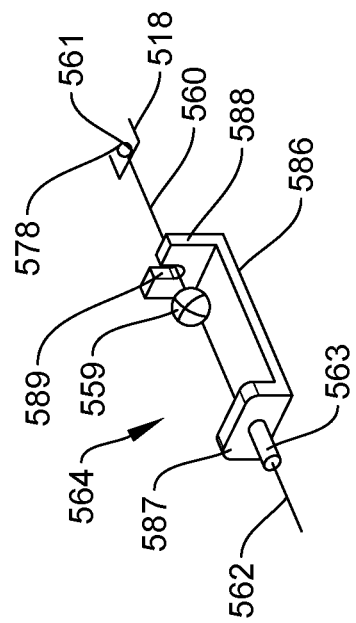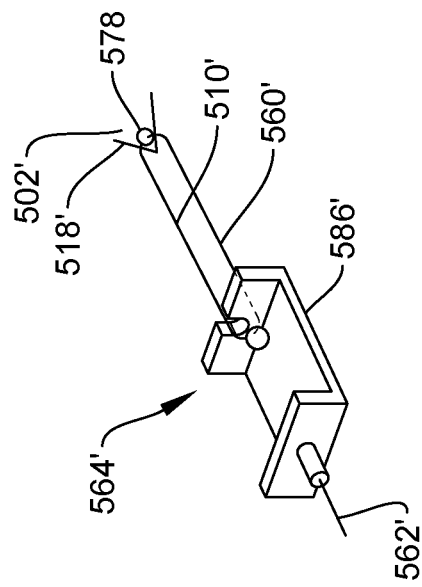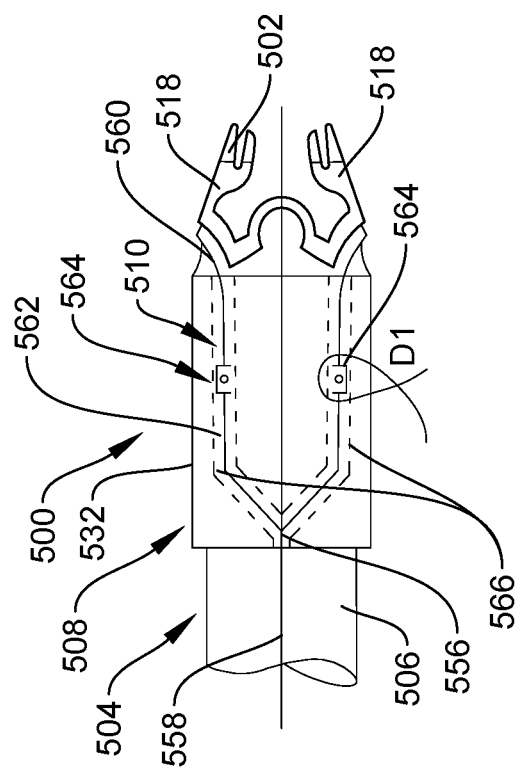

REPOSITIONABLE OVER THE SCOPE CLIP

PRIORITY CLAIM

The present disclosure claims priority to U.S. Provisional Patent Application Ser. No. 63/202,085 filed May 26, 2021; the disclosure of which is incorporated herewith by reference.

FIELD

The present disclosure relates to endoscopic devices and, in particular, relates to endoscopic clipping devices for treating tissue.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks).

Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient. In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue may determine that the distal end of the device and the clip are in a desired position relative to the target tissue. Based on the observation of the target tissue, the operator then deploys the clip without being able to see the clip itself until it is deployed. Once deployed, such current over-the scope clips are generally incapable of being repositioned.

SUMMARY

The present embodiments are directed to a clipping system for treating tissue, comprising an adapter extending longitudinally from a proximal end configured to be mounted over a distal end of an insertion device to a distal end and a clip including first and second jaws. A first end of the first jaw being is connected to a first end of the second jaw via a first hinge and a second end of the first jaw is connected to a second end of the second jaw via a second hinge so that the first and second jaws are movable between an insertion configuration, in which the clip is mounted over the adapter so that the first and second jaws are separated from one another to receive tissue therebetween, and an initial deployed configuration in which the first and second jaws are drawn toward one another to grip tissue therebetween, at least one of the first and second hinges being biased to draw the clip toward the initial deployed configuration. A first extending member is releasably coupled to the clip and movably connected to the adapter to permit a movement of the clip relative to the adapter from the insertion configuration to the initial deployed configuration. The first extending member is configured to permit withdrawal of the adapter proximally away from the clip while the extending member remains coupled to the clip to place the system in a review configuration in which the clip is physically separated from the adapter to enhance a visual observation of the clip. The first extending member is operable to retract the clip proximally over the adapter so that the clip is forced open as the clip is retracted over the adapter freeing the clip from tissue on which it has been clipped. The first extending member is also configured to release the clip therefrom in a final deployed configuration, when the clip is observed to be clipped in a desired position.

In an embodiment, the system may further comprise a second extending member releasably coupled to the clip and movably connected to the adapter, the second extending member configured to remain coupled to the clip while the clip is moved toward the initial deployed configuration and while the system is moved to the review configuration, the second extending member being operable to cooperate with the first extending member to retract the clip proximally over the adapter from one of the review and initial deployment configurations, and to release the clip therefrom in the final deployed configuration.

In an embodiment, proximal ends of the first and second extending members may be connected to one another and to a control element extending proximally therefrom to a proximal end accessible to a user of the system.

In an embodiment, a distal portion of the adapter, over which the clip is mountable in the insertion configuration, may be tapered toward the distal end of the adapter so that reducing a tension along the first extending member causes the clip to slide distally along the distal portion of the adapter from the open configuration toward the initial deployed configuration.

In an embodiment, the distal portion of the adapter may include a flat portion along an exterior surface thereof for reducing a friction between the clip and the adapter when the clip is moved distally therealong from the open configuration toward the initial deployed configuration, and a projection extending radially inward from an interior surface of the distal portion of the adapter configured to engage a portion of the clip when the clip is moved from the initial deployed configuration toward the open configuration.

In an embodiment, the distal end of each of the first and second extending members may include a loop configured to be hooked over a portion of a corresponding one of the first and second hinges, the distal ends of each of the first and second extending members are biased radially away from a longitudinal axis of the adapter so that, when loops of the first and second extending members are hooked over the first and second hinges, respectively, the distal ends of the first and second extending members are restrained toward an engaging configuration, and when the distal ends of the first and second extending members are disengaged from the first and second hinges, the distal ends of the first and second extending members spring laterally outward to release the clip therefrom in the final deployed configuration.

In an embodiment, the first jaw may include an opening extending therethrough for engaging the first extending member.

In an embodiment, the first extending member may include an enlarged member releasably connected to the distal end of the first extending member, the first extending member releasably coupled to the opening of the first jaw via the enlarged member.

In an embodiment, the clip may be movable from the review configuration to the final deployed configuration by drawing the first extending member proximally relative to the adapter until the enlarged member is pressed proximally against the first jaw and a force exerted thereon exceeds a predetermined threshold value so that the enlarged member is disengaged from the distal end of the first extending member.

In an embodiment, the system may further comprise a strand connected to the enlarged member and extending proximally therefrom so that, the clip is movable from the review configuration to the final deployed configuration by pulling the strand proximally until the enlarged member is disengaged from the distal end of the first extending member.

In an embodiment, the first extending member may include a coil extending from a proximal end to a distal end, a wire extending from the distal end of the coil to be looped through the opening of the first jaw, a distal end of the wire releasably attached to the distal end of the coil so that the first jaw is releasably coupled to the clip via the wire.

In an embodiment, the first extending member may include a proximal portion and a distal portion connected to one another via a releasable connection, the distal portion connected to the clip via the opening extending through the first jaw.

In an embodiment, the releasable connection may include a holding element including a first end fixedly attached to the proximal portion of the first extending member and a second end releasably attached to the distal portion of the first extending member so that, when the holding element is moved distally past a distal end of the channel of the adapter, the distal portion of the first extending elements is released therefrom.

The present embodiments are also directed to a clipping system for treating tissue, comprising an endoscope including a shaft extending longitudinally from a proximal end to a distal end and an adapter including a proximal portion mounted over the distal end of the shaft of the endoscope and a distal portion extending distally from the proximal portion, the distal portion tapered toward a distal end thereof. A clip is configured to be mounted over the distal portion of the adapter, the clip including first and second jaws, a first end of the first jaw being connected to a first end of the second jaw via a first hinge and a second end of the first jaw being connected to a second end of the second jaw via a second hinge so that the first and second jaws are movable between an insertion configuration, in which the first and second jaws are separated from one another to receive tissue therebetween, and an initial deployed configuration in which the first and second jaws are drawn toward one another to grip tissue therebetween. At least one of the first and second hinges is biased to draw the clip toward the initial deployed configuration. First and second extending members are releasably coupled to the clip at distal ends thereof and movably connected to the adapter so that a longitudinal movement of the first and second extending members relative to the adapter moves the clip between the open insertion configuration, an initial deployed configuration, in which the clip is moved toward the closed configuration immediately distal of the adapter, a review configuration, in which the clip is separated from a distal end of the endoscope via a distance selected so that the clip is visible via the endoscope, and a final deployed configuration, in which the clip is released from the extending member in the closed configuration. A control element is connected to proximal ends of the first and second extending members to extend proximally therefrom.

In an embodiment, the system may further comprise a coil extending proximally from the adapter and configured to slidably receive the control element therein and an actuating assembly including a handle member and a spool mounted thereover and longitudinally movable relative thereto. The handle member may be connected to a proximal end of the coil and the spool may be connected to a proximal end of the control element so that the spool is moved relative to the handle member to move the clip between the open insertion configuration, the initial deployed configuration, the review configuration and the final deployed configuration.

The present embodiments are also directed to a method for treating tissue. A clip is inserted to a target area in a body lumen via an endoscope, the clip mounted over a distal end of an endoscopic shaft, via an adapter, in an open insertion configuration in which jaws of the clip are separated from one another. A suction force is applied through a working channel of the endoscope so that tissue is drawn into a channel of the adapter and between jaws of the clip. The clip is moved from the open insertion configuration to an initial deployed configuration by reducing a tension along extending member, distal ends of which are releasably coupled to the clip, so that the clip is permitted to slide distally along a tapered exterior surface along a distal portion of the adapter over which the clip is mounted. Extending members, distal ends of which are releasably coupled to the clip, are moved distally relative to the endoscopic shaft so that the clip is moved distally away from a distal end of the adapter toward a review configuration in which the clip is visible via the endoscope. The clip is moved from the review configuration to the final deployed configuration by releasing the clip from the extending members.

BRIEF DESCRIPTION

FIG. 1 shows a perspective view of a system according to an exemplary embodiment of the present disclosure;

FIG. 2 shows a perspective view of an adapter according to the system of FIG. 1;

FIG. 3 shows a side view of the adapter of FIG. 2;

FIG. 20 shows a partial longitudinal cross-sectional view of a distal portion of a system according to another exemplary embodiment of the present disclosure;

FIG. 21 shows a perspective view of a releasable coupling according to the system of FIG. 20;

FIG. 22 shows a perspective view of a releasable coupling according to an alternate embodiment of the system of FIG. 20;

DETAILED DESCRIPTION

Figure 4:
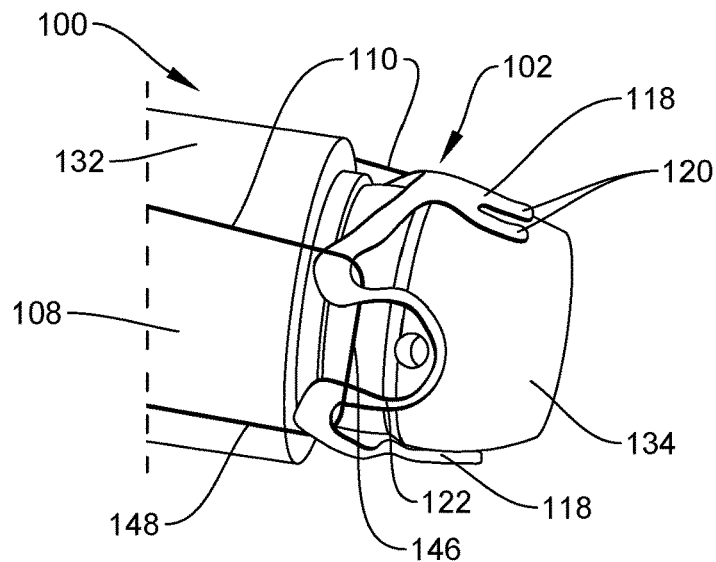
FIG. 4 shows a longitudinal side view of a distal portion of the system of FIG. 1, in an insertion configuration.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a final deployment thereof. Exemplary embodiments of the present disclosure comprise a clip mountable over a distal end of an endoscope via an adapter and releasably coupled to extending members so that the clip may be moved between an insertion configuration, an initial deployed condition and a review configuration in which the clip can be viewed prior to being finally deployed.

In the insertion configuration, the clip is mounted over the adapter in a proximal position maintained in the insertion configuration ready to receive tissue between jaws thereof while the clip's position minimizes its occlusion of the field of view of the endoscopic vision system. The insertion configuration is configured to facilitate insertion of the endoscope to a target site adjacent to tissue to be clipped while the system allows the clip to be deployed and clipped over tissue in an initial deployed configuration. The device permits the endoscope to be withdrawn proximally away from the clip and the tissue over which it is clipped while the clip remains coupled to the device in a review configuration. As the endoscope is withdrawn proximally while the clip remains in place over the target tissue, the field of view of the vision system of the endoscope widens to show the clip and the tissue clipped thereby so that the operator can determine whether the position of the clip is desirable or in need of adjustment.

If the operator determines that the clip is positioned as desired, the clip is deployed and left in place clipped over the target tissue. If the operator determines that the position of the clip needs adjustment, the endoscope and the adapter coupled thereto are moved distally to a position adjacent to the clip. The clip is then drawn proximally over the adapter to reopen the clip which is drawn proximally over the distal end of the adapter forcing the clip to open against its natural bias as the clip slides proximally back over the adapter to return to the insertion configuration. After the clip has been removed from the tissue and returned to the insertion configuration, the operator can re-position the endoscope and device as desired, draw target tissue into the adapter (e.g., under suction or a grasper applied via a working channel of the endoscope) and once more deploy the clip from the adapter over the target tissue in the initial deployed position. The endoscope is then withdrawn proximally once again as the clip remains coupled to the device so that the device moves again into the review configuration.

The position of the clip and the clipped tissue are again observed and, this process may be repeated until the clip is positioned as desired. When the operator sees that the tissue over which the clip is closed is the desired portion of tissue, the clip may be deployed and released from the device and endoscope as described below. It will be understood by those of skill in the art that terms proximal and distal, as used herein, are intended to refer to a direction toward and away from, respectively, a user of the device.

FIGS. 1-10 show a clipping system 100 for treating tissue defects and/or perforations according to an exemplary embodiment of the present disclosure. As shown in FIG. 1, the clipping system 100 comprises a clip 102 configured to be mounted to a distal end 106 of an endoscopic shaft of an endoscope 104 via an adapter 108. The clip 102 is releasably coupled to a pair of extending members 110 configured so that, when moved relative to the endoscopic shaft 124, the extending members 110 move the clip 102 between an insertion configuration, an initial deployed configuration, a review configuration, and a final deployed configuration.

In the insertion configuration, the clip 102 is mounted over the adapter 108 so that the adapter 108 holds the clip 102 in an open position with jaws 118 of the clip 102 spread apart from one another so that tissue to be clipped may be drawn through the clip 102 between the jaws 118. As described below, the clip 102 may be pushed distally from the insertion configuration to an initial deployed configuration by via a deployment element that pushes the clip 102 distally along and off of the adapter 108 until the clip 102 moves distally off of the adapter 108. At this point, the resistance that had been provided by the adapter 108 to the closing of the jaws 118 is removed and the jaws 118 spring closed under a natural bias of the clip 102 (e.g., in hinges 122).

In this initial deployed configuration the clip 102 remains connected to the system 100 via the extending members 110. The adapter 108 and the clip 102 may then be physically separated to move the system 100 into the review configuration. As described in more detail below, tissue may be drawn into the clip 102 when the clip 102 is in the insertion configuration. When the operator believes a desired portion of tissue (i.e., the tissue to be clipped) has been drawn into the clip 102, the clip 102 may be moved distally off of the adapter 108 so that the jaws 118 spring closed over the tissue drawn through the clip 102 to clip this tissue. This clip 102 remains coupled to the system 100 via the extending members while the endoscope 104 and the adapter 108 may be moved proximally away from the clip 102 that remains clipped over tissue. This permits the operator to expand the field of view of the endoscope so that the clip 102 and the clipped tissue may be viewed more clearly and tissue surrounding the clip 102 and the clipped tissue may also be viewed to determine if the clip 102 is clipped over the target tissue as desired. This configuration in which the adapter 108 and the endoscope 104 have been withdrawn proximally relative to the clip 102 to better observe the clip 102 is the review configuration.

For example, in the review configuration, the clip 102 is moved distally relative to the adapter 108 to separate the clip 102 from the distal end 106 of the endoscopic shaft 124 by a distance selected so that the view of the clip 102 provided to the operator via the optical system of the endoscope 104 enables the operator (e.g., surgeon) to confirm whether the clip 102 is clipped over the target tissue, as desired. If desired, the operator may also view the clip from different perspectives to the extent this is permitted by the surrounding tissue. If the user determines that the clip 102 is not clipped over the target tissue as desired, the user may move the endoscope 104 distally over the extending members 110 so that the distal end of the adapter 108 approaches and eventually contacts the proximal side of the clip 102. Contact between the distal end of the adapter 108 and the proximal side of the clip 102 and increased tension applied to the extending members 110 move the clip proximally over the adapter 108 so that the jaws 118 are forced apart and the clip returns to the insertion configuration.

When the jaws 118 are opened, the clip 102 is freed from the clipped tissue so that the clip 102 may be repositioned relative to the target tissue. The process may then be repeated until the operator confirms that the clip 102 is clipped over the target tissue, as desired. At this point, the operator may move the clip 102 from the review configuration to the final deployed configuration by disengaging the clip 102 from the extending members 110, as will be described in further detail below. As will also be described in further detail below, movement of the clip 102 between the insertion configuration, the initial deployed configuration, the review configuration and the final deployed configuration may be controlled via an actuating assembly 112 at a proximal end of the endoscopic shaft 124.

The clip 102 may be mounted to any standard endoscope 104 via the adapter 108 which is sized, shaped and configured to be mounted over the distal end 106 of the endoscopic shaft 124 of the endoscope 104. As will be understood by those of skill in the art, the endoscopic shaft 124 is configured to be inserted through a body lumen to a target area within the lumen and thus, must be sufficiently flexible to navigate through even tortuous paths of the body lumen. As shown in FIGS. 2-3, the adapter 108 extends from a proximal end 126 to a distal end 128 and includes a channel 130 extending therethrough.

In one embodiment, the adapter 108 is substantially tubular, having a circular cross-sectional area. A proximal portion 132 of the adapter 108 is configured to be mounted over the distal end 106 of the endoscopic shaft 124 while a distal portion 134 of the adapter 108 is configured to receive the clip 102 thereover, in the insertion configuration. Thus, an inner diameter of the channel 130 along the proximal portion 132 of the adapter 108 is sized, shaped and configured to correspond to an outer diameter of the endoscopic shaft 124 at the distal end 106 so that the adapter 108 may be mounted thereover via, for example, a friction fit. An outer diameter of the distal portion 134 is sized, shaped and configured to receive the clip 102 thereover, in the open configuration, as will be described in further detail below.

In one exemplary embodiment, the distal portion 134 tapers from a larger outer diameter at a proximal end 135 thereof to a smaller outer diameter at the distal end 128 of the adapter 108 and may include a plurality of longitudinally extending flat portions 152 distributed about the circumference of an exterior surface 136 of the adapter 108. Each of the flat portions 152 extends along at least a portion of a length of the distal portion 134 and covers a portion of a perimeter (e.g., circumference) of the distal portion 134.

In one example, the exterior surface 136 includes four flat portions 152 distributed around the circumference of the distal portion 134. In this embodiment, flat portions 152 are equally sized and are separated from one another about the circumference of the distal portion 134. It will be understood by those of skill in the art that these flat portions 152 reduce friction between the clip 102 and the distal portion 134 of the adapter 108 to facilitate a movement of the clip 102 between the insertion configuration and the initial deployed configuration as will be described in further detail below. Although the adapter 108 is shown and described as including four equally spaced flat surfaces 152 along the exterior surface 136 of the distal portion 134, those skilled in the art will understand that the adapter 108 may include any number of flat surfaces 152 along the distal portion 134 distributed around the circumference of the adapter 108 in any of a variety of configurations so long as the flat surfaces 152 facilitate movement of the clip 102 distally along and off the distal portion 134 of the adapter 108 and also facilitate the drawing of the clip 102 from the initial deployed configuration proximally back onto the adapter 108 and proximally thereover to the insertion configuration. The distal portion 134 of this embodiment also includes a plurality of projections 144 extending radially into the channel 130 of the adapter 108 from curved portions 153 of the distal portion 134, which extend between adjacent flat portions 152.

In one exemplary embodiment, a distal face 154 of each these curved portions 153 is angled with respect to a longitudinal axis of the adapter 108 so that, when the clip 102 is drawn proximally from the initial deployed configuration so that the jaws 118 abut the distal face 154, the angle of these projections 144 facilitates the re-opening of the jaws 118 against their natural bias. The projections 144 may assist in alignment of an orientation of the clip 102 relative to the adapter 108. That is, the jaws 118 slide proximally over the projections 144 to open the jaws 118 so that the clip 102 is released from the clipped tissue and can be slid proximally back onto the adapter 108 to the insertion configuration.

In another embodiment, the adapter 108 includes a tab 138 extending from the exterior surface 136 of the adapter 108 toward the distal end 128 thereof so that a groove 140 is formed between the tab 138 and the exterior surface 136 along the distal portion 134. In the insertion configuration, the clip 102 of this embodiment is mounted over the distal portion 134 with one of the jaws 118 is received within the groove 140. The tab 138 also includes a hole 142 extending therethrough. The hole 142 is configured to receive a deployment element (not shown) such as, for example, a thread, strand or other similar element, which is used to move the clip 102 from the insertion configuration proximally along and off of the adapter 108 to the initial deployed configuration. A first end of the deployment element may, for example, be knotted or otherwise anchored to the tab 138 via the hole 142 so that the deployment element extends from the tab 138, across the groove 140 and through a working channel of the endoscope 104 via the channel 130 of the adapter 108 to a second end coupled to the proximal assembly 112.

In one exemplary embodiment, the deployment element extends into the channel 130 via an opening of the channel 130 at the distal end 128 of the adapter 108. In another embodiment, the deployment element extends into the channel 130 via a corresponding hole 174 extending through a wall of the distal portion 134 of the adapter 108. The corresponding hole 174 is, in this embodiment, coaxially aligned with the hole 142 extending through the tab 138, and is in communication with the channel 130. In the insertion configuration, the deployment element is slackened and extends across the groove 140 from the tab 138 to the working channel of the endoscope 104 proximally of a portion of the clip 102. When it is desired to move the clip 102 from the insertion configuration to the initial deployed configuration, the operator applies tension to the deployment element so that the tensioned deployment element moves distally against the clip 102 to push the clip 102 distally off of the adapter 108.

Although the exemplary embodiments show and describe the adapter 108 as including the tab 138, in some embodiments, the distal portion 134 of the adapter 108 may be sufficiently tapered from the proximal end 135 thereof to the distal end 128 of the adapter 108 so that the adapter 108 does not require the tab 138 to move the clip 102 from the open insertion configuration to the initial deployed configuration. Rather, the taper of the distal portion 134 portion biases the clip 102 toward the initial deployed configuration. The clip 102, however, may be remain mounted over the distal portion 134 in the open configuration so long as a sufficient proximally directed tension is applied to the extending members 110 so that the extending members 110 hold the clip 102 in place on the adapter 108. If this tension is removed from the extending members 110, the natural bias of the clip 102 draws the jaws 118 toward one another pushing the clip 102 distally over the tapered surface of the adapter 108 until the clip 102 slides off of the distal end of the adapter 108 as the extending members 110 are drawn distally with the clip 102. As the extending members 110 move distally relative to the endoscopic shaft 124 and tension therealong is reduced, the clip 102 is permitted to slide distally along the distal portion 134 toward the initial deployed configuration.

The clip 102 includes a pair of jaws 118 connected to one another via hinges 122 which permit movement of the jaws 118 relative to one another between the open configuration, in which the jaws 118 are separated from one another, to the closed configuration, in which the jaws 118 are moved toward one another. Each of the jaws 118 may extend along a curve from a first end 125 to a second end 127 so that the first ends 125 of the jaws 118 are connected to one another via a first one of the hinges 122 and the second ends 127 of the jaws 118 are connected to one another via a second one of the hinges 122.

According to one exemplary embodiment, each the hinges 122 may be a living hinge that is substantially C-shaped, a curve of the C-shape extending toward and between the pair of jaws 118. The hinges 122 may be spring biased, biasing the jaws 118 toward the closed configuration. In one exemplary embodiment, each of the jaws 118 include gripping features 120 such as, for example, teeth, so that when the jaws 118 are moved toward one another toward the closed configuration, tissue may be gripped between the jaws 118 via the gripping features 120.

Figure 5:
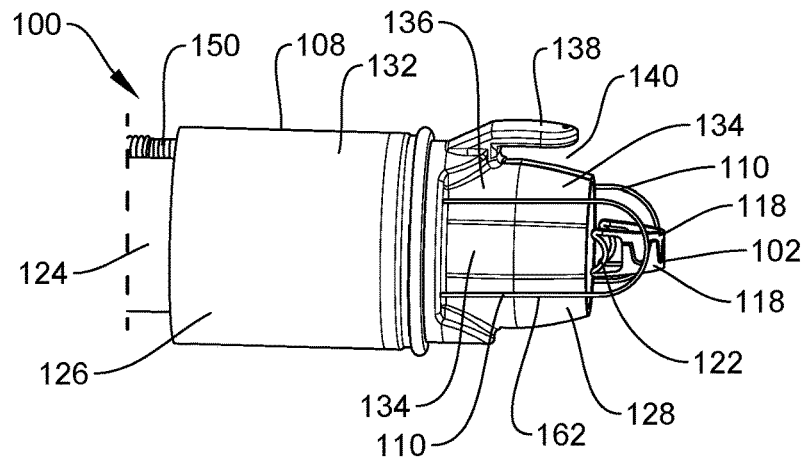
FIG. 5 shows a longitudinal side view of the distal portion of the system of FIG. 1, in an initial deployed configuration.
Figure 6:
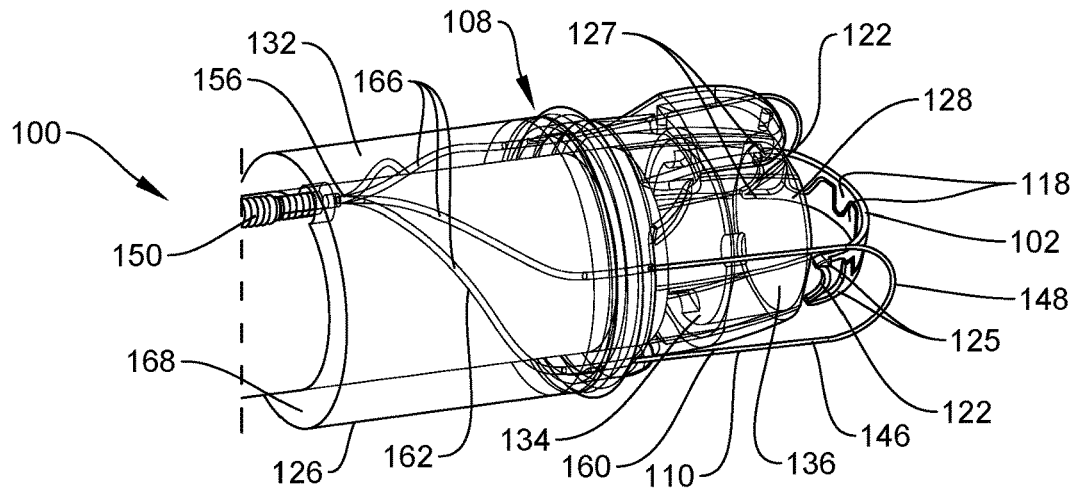
FIG. 6 shows a transparent perspective view of the distal portion of the system of FIG. 1, in the initial deployed configuration.

Since each of the jaws 118 extends along a curve, when the clip 102 is mounted over the distal portion 134 of the adapter 108 in the insertion configuration, as shown in FIG. 4, each of the jaws 118 extends about diametrically opposing portion of the adapter 108 so that the exterior surface 136 of the adapter 108 maintains the clip 102 in the open configuration. In the open configuration, the jaws 118 are separated from one another so that target tissue may be drawn into the adapter between the jaws 118 for clipping. When the clip 102 is moved distally off the adapter 108, the clip 102 is freed to revert to close (due to the bias of the clip 102) over tissue drawn into the adapter (e.g., via suction or a grasping device inserted through a working channel of the endoscope 104), as shown in FIGS. 5-6. Thus, where the distal portion 134 is sufficiently tapered, the clip 102 is held in the insertion configuration by proximally directed tension applied to the extending members 110 which are coupled to the clip 102 and apply a proximally directed force thereto.

Releasing tension from the extending members 110 permits the clip 102 to slide distally along the distal portion 134 as the bias of the clip 102 pulls the jaws 118 toward one another dragging the clip 102 distally over the adapter until the clip 102 moves off the distal end 128 of the adapter 108 allowing the jaws 118 to snap shut over the tissue that had been drawn into the adapter 108 to reach the initial deployed configuration immediately distal of the distal end 128 of the adapter 108. It will be understood by those of skill in the art that the hinges 122 and/or jaws 118 of the clips 102 may be formed of any of a variety of materials so long as the hinges 122 bias the jaws 118 toward the closed configuration, as described above. In one example, portions of the clip 102 (e.g., the hinges 122) may be formed of a shape memory alloy such as, for example, Nitinol.

As described above, movement of the clip 102 between the insertion configuration, the initial deployed configuration, the review configuration and the final deployed configuration is facilitated via the extending members 110 which are releasably coupled to the clip 102. In one exemplary embodiment, the extending members 110 are releasably coupled to the hinges 122 of the clip 102. In this embodiment, the clipping system 100 includes two extending members 110, each of which extends from a distal end 148, releasably coupled to a corresponding hinge 122 of the clip 102, to a proximal end 156. Proximal ends 156 of the two extending members 110 are connected to one another and to a control element 158, which extends proximally therefrom to the actuating assembly 112. The extending members 110 and/or the control element 158 may be comprised of flexible strands, filaments or coils formed of, for example, a metal or polymer as would be understood by those skilled in the art.

Figure 8:
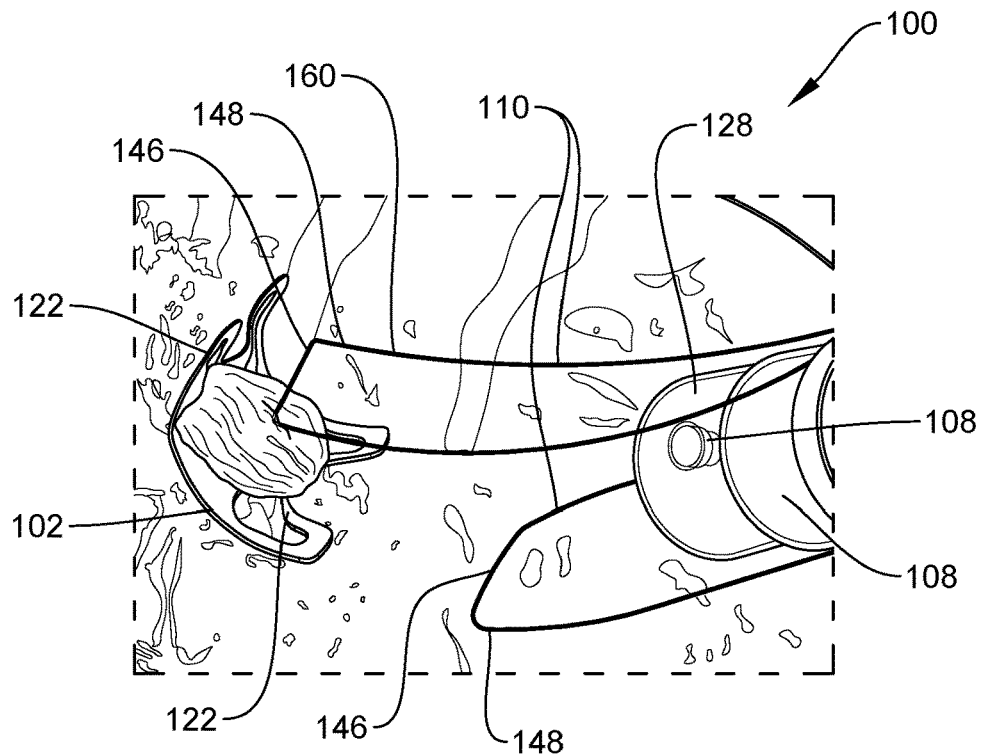
FIG. 8 shows a perspective view of the distal portion of the system of FIG. 1, in a final deployed configuration.

In one exemplary embodiment, distal portions 160 of the pair of extending member 110 extend along opposing sides of the distal portion 134 of the adapter 108 so that each of the extending members 110 engages a corresponding one of the hinges 122 of the clip 102. In one exemplary embodiment, each distal portion 160 of the pair of extending members 110 forms a loop 146 at the distal end 148 thereof for engaging the C-shaped hinge 122 of the clip 102. Each loop 146 is hooked over the C-shaped portion of the corresponding one of the hinges 122 so that the loops 146 engage the hinges 122 via, for example, a friction fit. The distal ends 148 of the extending members 110 in this embodiment are biased to move (when unconstrained) away from a longitudinal axis of the adapter 108, as shown in FIG. 8, and radially away from the clip 102 to a release configuration. That is, when the extending members 110 are disengaged from the clip 102, the extending members 110 spring radially away from the clip 102 to fully disengage from the clip 102 so that the endoscope 104, the adapter 108 and the extending members 110 may be removed from the body while leaving the clip 102 in the final deployed configuration clipped over the target tissue.

When coupled to the clip 102, the loops 146 are hooked over the C-shaped hinges 122 so that the distal ends 148 of the extending members 110 are prevented from springing radially outward and so remain in engagement with the C-shaped hinges 122. When the clip 102 is determined to be in a desired position clipped over target tissue (e.g., when an operator observing the clip 102 from the review configuration determines the clip 102 is positioned as desired) the adapter 108 and the endoscope 104 are advanced distally over the extending members 110 until the adapter contacts the clip 102 or is positioned adjacent thereto. At this point, the extending members 110 are extended distally.

As the clip 102 is prevented from moving further distally by the tissue over which it is clipped, further distal pressure applied to the extending members 110 moves the loops 146 distally (e.g., overcoming the friction of the loops' friction fits to the clip 102) until the loops 146 pass the distal ends of the C-shaped hinges 122. At this point, the loops 146 are no longer constrained by the hinges 122 and the loops 146 spring radially outward away from the clip 102 finally separating the clip 102 from the system 100 and leaving the clip in the finally deployed configuration. It will be understood by those of skill in the art that when the distal ends 148 are no longer constrained by the hinges 122, the loops 146 move apart from one another so that a distance between the distal ends 148 is greater than when the distal portion 160 of the extending members 110 were restrained by the clip 102.

While the distal portions 160 of the extending members 110 extend alongside the exterior surface 136 of the distal portion 134 of the adapter 108, proximal portions 162 of the extending members 110 extend through corresponding channels 166 extending longitudinally through a wall 168 of the of the proximal portion 132 of the adapter 108, as shown in FIG. 6. In one embodiment, the proximal portion 132 includes four channels 166 for accommodating the two strands which form each of the loops 146. The channels 166 extend through the wall 168 to converge at a point at which the proximal ends 156 of the extending members 110 connect to one another and to the control element 158. The channels 166 are configured to slidably receive portions of the extending members 110 so that longitudinal movement of the control element 158 relative to the endoscopic shaft 124 moves the extending members 110 distally and/or proximally to move the clip 102 between the open insertion configuration, the initial deployed configuration, the viewing configuration and the final deployed configuration.

In one exemplary embodiment, the control element 158 extends translationally through a coil 150 extending between the adapter 108 and the actuating assembly 112. The coil 150 may extend from, for example, the proximal end 126 of the adapter 108 to extend alongside the endoscopic shaft 124. The coil 150 may be coated with a material (e.g., PTFE) to reduce friction between the endoscopic shaft 124 and the coil 150, which may or may not be braided. It will be understood that the coil 150 remains longitudinally fixed relative to the endoscopic shaft 124 while the control element 158 is longitudinally movable relative thereto to facilitate movement of the extending members 110. The control element 158 may be similarly coated with a friction reducing material such as, for example, PTFE/MDX, to reduce friction between the coil 150 and the control element 158.

In the insertion configuration, as shown in FIG. 4, the control element 158 maintains a desired proximally directed tension therealong so that the clip 102, which is releasably coupled to the extending members 110 remains mounted over the adapter 108 in the open configuration. When it is desired to clip tissue, tissue is drawn into the distal end of the adapter 108 (e.g., by applying suction or a grasping element through a working channel of the endoscope 104) and the control element 158 is moved distally relative to the coil 150 and the endoscopic shaft 124 to reduce the proximal tension from the control element 158. This permits the clip 102 to slide distally along the tapered exterior surface 136 until the clip 102 moves distally off the distal end 128 of the adapter 108 to spring closed over the tissue that had been drawn into the adapter 108. At this point, the clip 102 is in the initial deployed configuration closed over this tissue immediately distal of the distal end 128 of the adapter 108, as shown in FIGS. 5-6.

Figure 7:
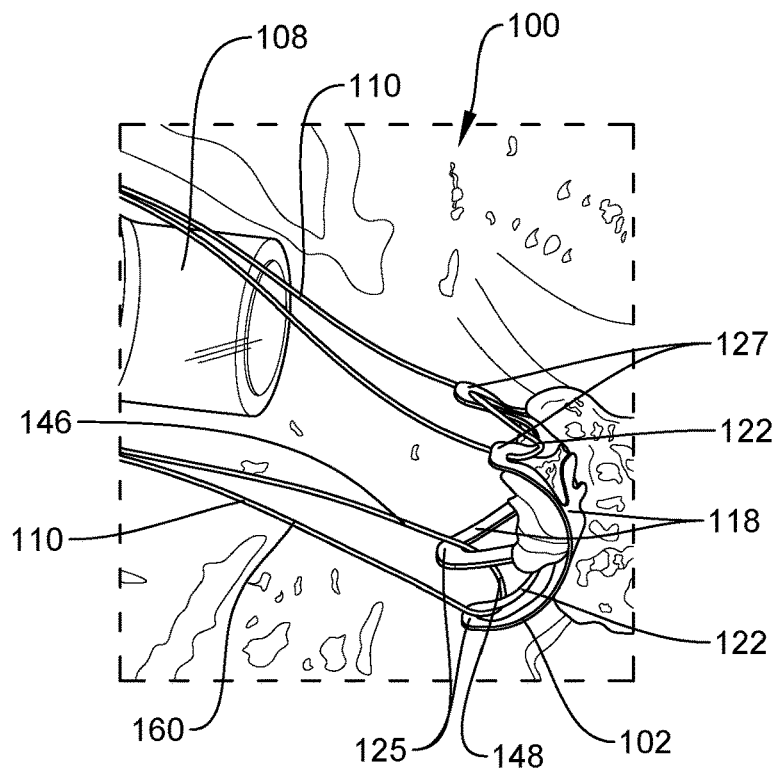
FIG. 7 shows a perspective view of the distal portion of the system of FIG. 1, in a review configuration.

To move the system 100 to the review configuration, as shown in FIG. 7, the coil 150 is moved proximally relative to the control element 158 so that the endoscopic shaft 124 slides proximally over the extending members 110 and the adapter 108 moves proximally relative to the clip 102. When the clip 102 is separated from the distal end 106 of the endoscopic shaft 124 via a distance selected so that the clip 102 is visible via the endoscope 104 (to the extent permitted by surrounding anatomy), the operator views the clip 102, the clipped and surrounding tissue.

If, upon viewing, it is desired to adjust a position/placement of the clip 102, the endoscope 104 and the adapter 108 are slid distally over the extending members 110 until the projections 144 at the distal end of the adapter 108 contact the clip 102. Proximally directed tension applied to the extending members at this point, draws the clip 102 against the projections 144 so that the angled surfaces of the projections 144 force the jaws 118 apart against their natural bias as the jaws 118 and the clip 102 move proximally over the adapter 108. When the jaws 118 are fully opened, the clipped tissue is released and the clip 102 may be drawn proximally over the adapter 108 to the insertion configuration. That is, the column strength of the endoscope 104 and the adapter 108 apply a distal force (Via the distal end 128 of the adapter 108) to the jaws 118 as the proximally directed tension in the extending members 110 draws the clip proximally against the projections 144 forcing the jaws 118 to open so that as the clip 102 is drawn further proximally relative to the adapter 108. The operator may then reposition the clip 102 as desired and repositioned and repeat this process until the clip 102 is clipped over tissue as desired. When the operator confirms that the clip 102 has been deployed as desired, the system 100 may release the clip 102 in the final deployed configuration as described above.

According to one exemplary embodiment, when it is desired to release the clip 102 from the extending members 110 in the final deployed configuration, as shown in FIG. 8, the extending members 110 are moved distally relative to the clip 102 (via the control element 158) until the loops 146 are moved distally out of engagement with the hinges 122 as described above. As the loops 146 are moved distally of, for example, the C-shaped hinges 122, and out of engagement therewith, the distal ends 148 of the extending members 110 are released from the hinges 122 and permitted to revert to their biased configuration, in which the distal ends 148 move radially away from one another. Since the distal ends 148 extend radially away from one another, the extending members 110 are no longer coupled to the clip and may be moved proximally away from the clip 102 without re-engaging the clip 102. Thus, the clip 102 may be left within the body, clipped to the target tissue, while the endoscope 104 is removed therefrom.

It will be understood by those of skill in the art that although the clip 102 is described and shown as having C-shaped hinges 122, the clip 102 the hinges 122 may have any of a variety of shapes and configurations so long as the hinges 122 are configured to bias the jaws 118 of the clip 102 toward the closed configuration, as described above. Similarly, it will be understood by those of skill in the art that the distal ends 148 of the extending members 110 may have any of a variety of shapes and configurations so long as the distal ends 148 are configured to releasably engage the hinges 122, as described above.

Figure 9:
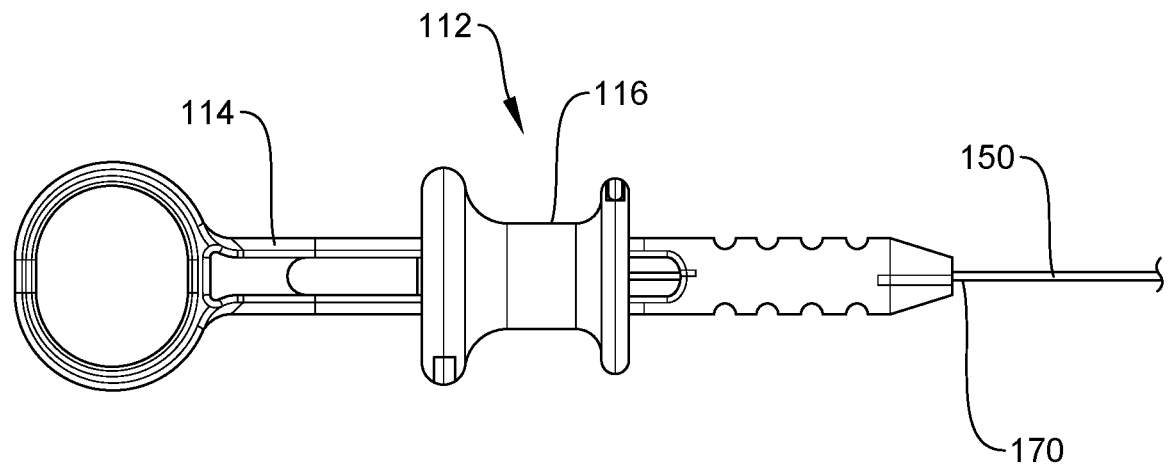
FIG. 9 shows longitudinal side view of an actuating assembly of the system of FIG. 1.
Figure 10:
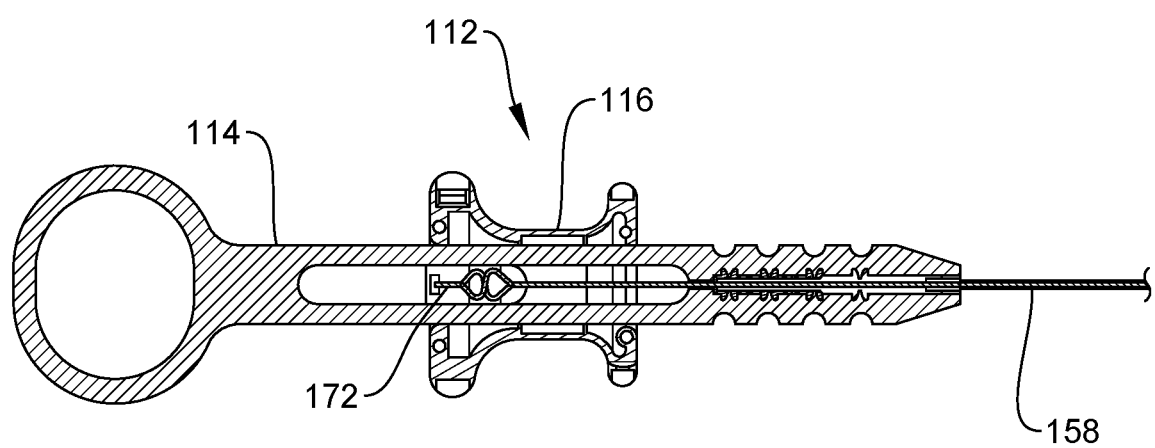
FIG. 10 shows a longitudinal cross-sectional view of the actuating assembly of the system of FIG. 1.
Figure 11:
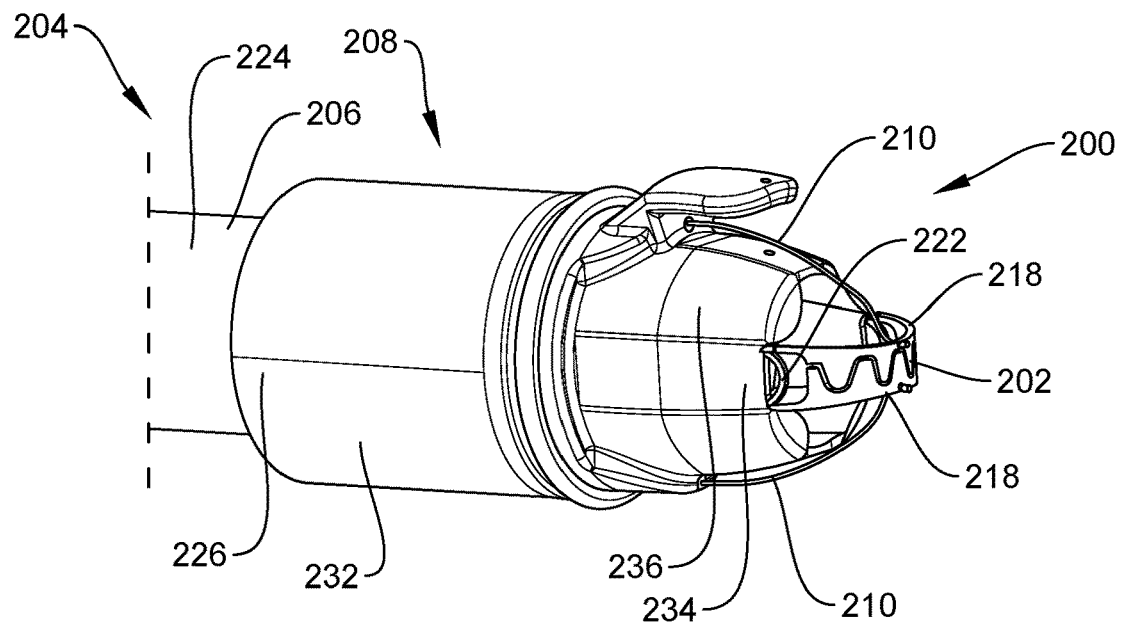
FIG. 11 shows a perspective view of a distal portion of a system according to another exemplary embodiment of the present disclosure.
Figure 12:
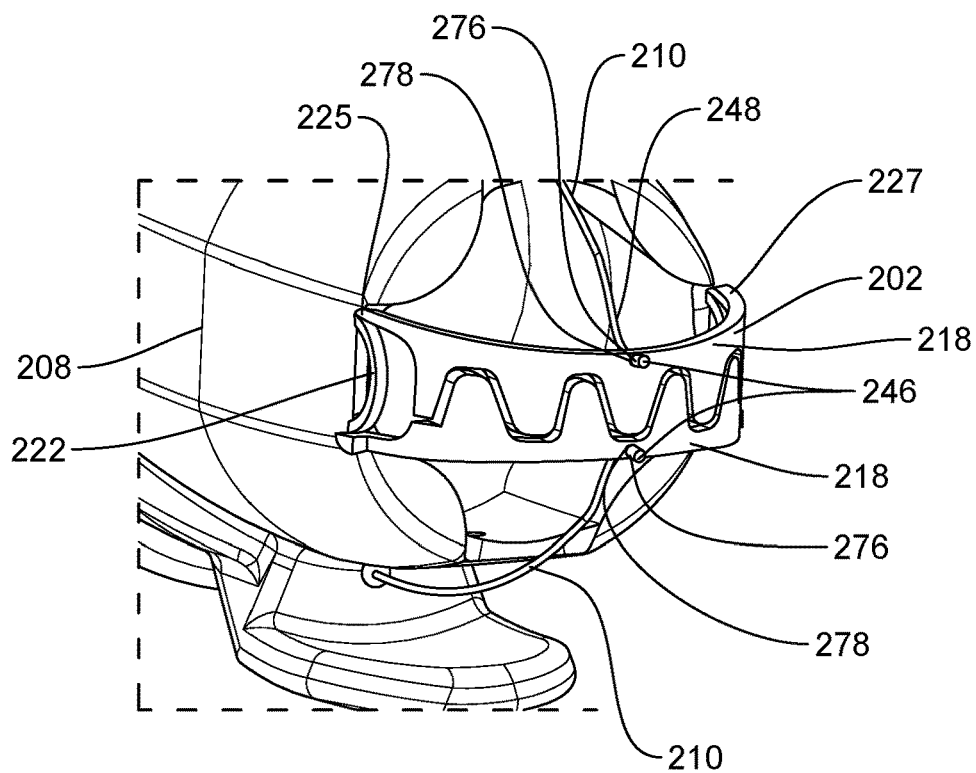
FIG. 12 shows an enlarged perspective view of the distal portion of the system of FIG. 11.
Figure 13:
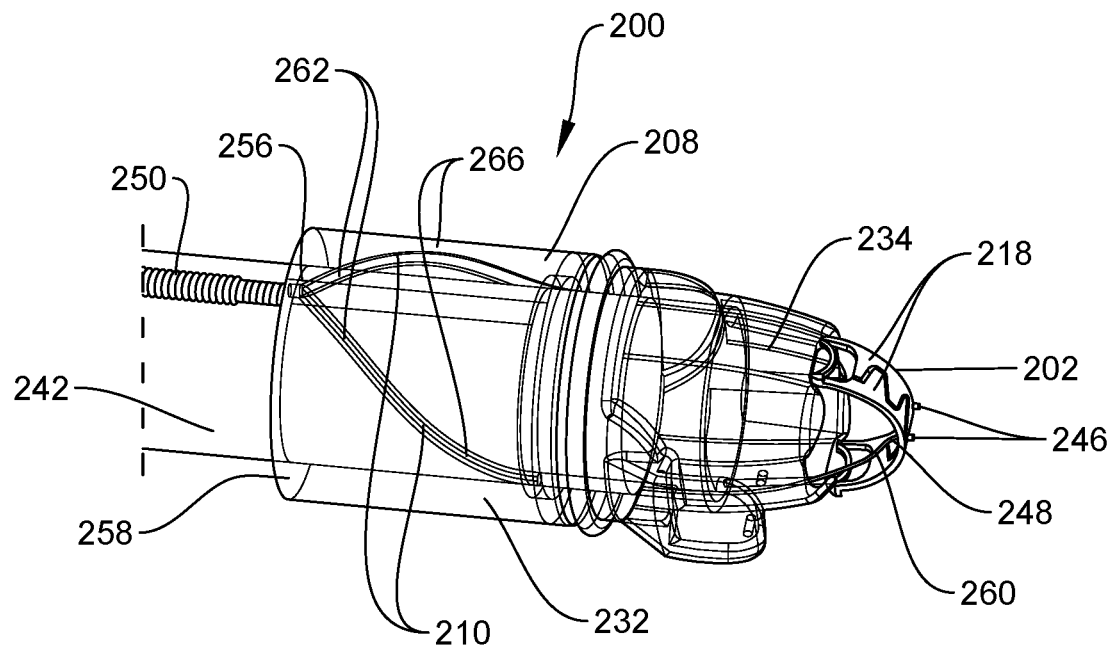
FIG. 13 shows a partially transparent perspective view of the distal portion of the system of FIG. 11.
Figure 14:
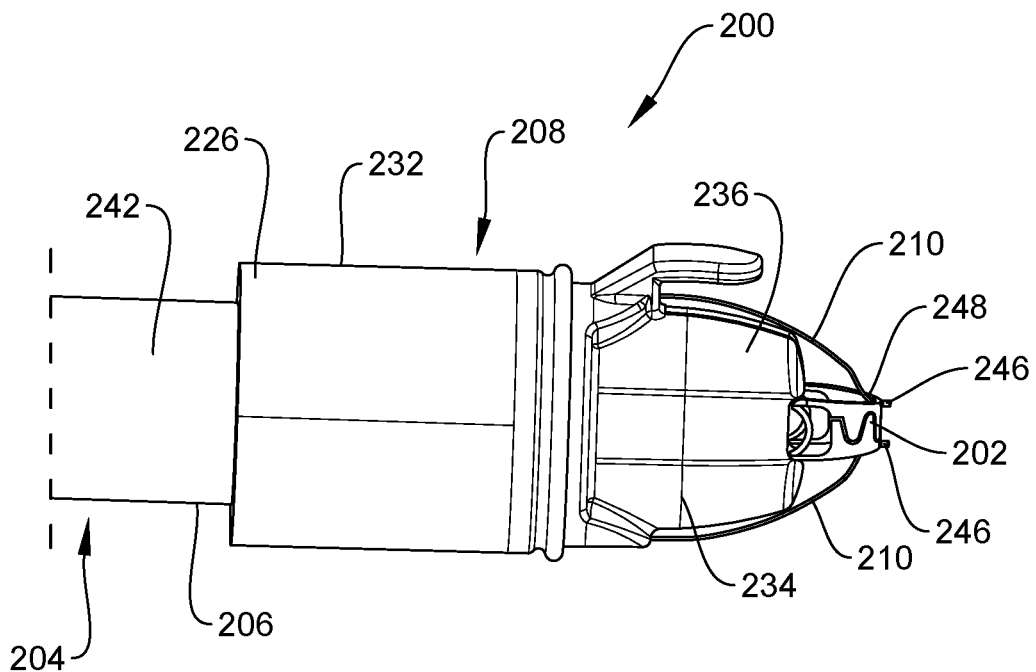
FIG. 14 shows a longitudinal side view of the distal portion of the system of FIG. 11.

As described above, the actuating assembly 112 may be used to move the extending members 110 relative to the endoscopic shaft 124 to move the clip 102 between the insertion configuration, the initial deployed configuration, the review configuration and the final deployed configuration. As shown in FIGS. 9-10, the actuating assembly 112 comprises a handle member 114 and a spool 116 slidably mounted thereover. The handle member 114 is connected to a proximal end 170 of the coil 150, while the spool 116 is connected to a proximal end 172 of the control element 158. Thus, the spool 116 may be moved relative to the handle member 114 to correspondingly move the control element 158 relative to the coil 150, thereby moving the clip 102 relative to the endoscope 104 between the open insertion configuration, the initial deployed configuration, the viewing configuration and the final deployed configuration, as described above.

According to an exemplary method for tissue closure utilizing the clipping system 100, the distal end of an endoscope 104 including an adapter 108 and a clip 102 as described, are inserted into a living body (e.g., via a body lumen (e.g., GI tract) accessed, for example, by a naturally occurring body orifice) to a target area within the body lumen adjacent to tissue to be clipped. As described above, in the insertion configuration, as shown in FIG. 4, the clip 102 is mounted to the distal end 106 of the endoscopic shaft 124 via the adapter 108, so that the jaws 118 are separated from one another in the insertion configuration.

As would be understood by those skilled in the art, the clip 102 is guided to the target area via the endoscope 104 (e.g., using a vision system of the endoscope 104) and positioned adjacent to target tissue. A portion of tissue is drawn into the channel 130 of the adapter 108 (e.g., via a suction force or a grasping instrument applied through a working channel of the endoscope 104) so that the target tissue may be drawn into the channel 130 of the adapter 108. The clip 102 is then moved distally over and off of the adapter 108 so that the jaws 118 spring shut and the clip 102 is clipped over the tissue in the channel 130, as shown in FIGS. 5-6. As described above, the clip 102 may be moved toward distally over the adapter 108 by, for example, moving the spool 116 distally relative to the handle member 114 so that the clip 102 is permitted to slide distally along the tapered exterior surface 136 of the distal portion 134 of the adapter 108 and the jaws 118 of the clip 102 are permitted to close under their biased to the initial deployed configuration.

It will be understood by those of skill in the art that suctioning and/or gripping of the tissue in this initial deployed configuration obstructs an imaging/optical lens of the endoscope 104 so that the user is no longer able to visualize and/or confirm whether a desired portion of tissue (i.e., the target tissue) has been properly clipped. Distancing the clip 102 from the distal end 106 of the endoscopic shaft 124, however, eliminates this obstruction by separating the clipped tissue from the distal end of the endoscope 104 so that an operator can observe the clip 102 and the clipped tissue. When in the initial deployed configuration, the clip 102 may be moved toward the viewing configuration, as shown in FIG. 7, by moving the endoscopic shaft 124 proximally with respect to the clip 102 by, for example, moving the handle member 114 proximally with respect to the spool 116 while the extending members 110 are allowed to play out until the clip 102 is separated from the endoscope 104 sufficiently to make the desired observations. In particular, moving the coil 150 proximally relative to the extending members 110, allows the endoscope 104 to be drawn proximally away from the clip 102, creating distance between the clip 102 and the distal end 106 of the endoscopic shaft 124 selected so that the clip 102 may be visualized via the optical system of the endoscope 104.

If, upon visualization, the user determines that the clip 102 requires an adjustment and/or a repositioning relative to the target tissue, the endoscope 104 is slid distally over the extending members 110 by, for example, moving the handle member 114 distally while holding the spool 116 stationary, until the distal end 128 of the adapter 108 is adjacent to the clip 102. The extending members 110 may then be drawn proximally to pull the clip 102 over the distal portion 134 of the adapter 108 to the insertion configuration releasing the clipped tissue, as described above.

The clip 102 may then be repositioned relative to the target tissue and this new tissue may be drawn into the channel 130 of the adapter 108 as described above. The clip 102 may then be moved distally off of the adapter 108 to clip this new portion of tissue in the same manner described above. The system 100 may be moved again to the review configuration and, if the operator determines that the desired tissue is clipped as desired, the clip 102 may be moved to the final deployed configuration as described above. This process may be repeated, as many times as necessary, until the user confirms that the clip 102 has been clipped over the target tissue, as desired.

Once the user confirms that the target tissue has been clipped, as desired, the clip 102 may be moved from the review configuration to the final deployed configuration, as shown in FIG. 8, by releasing the clip 102 from the extending members 110. As described above, to release the clip 102, the control element 158, and thereby the extending members 110, are moved further distally relative to the endoscopic shaft 124. Since in the review configuration the clip 102 is clipped over the target tissue and thereby abuts a tissue surface, moving the extending members 110 further distally causes the extending members 110 to also be moved distally relative to the clip 102. The extending members 110 are moved distally relative to the clip 102 until the distal ends 148 of the extending members 110 disengage the hinges 122 of the clip 102.

According to one embodiment, the extending members 110 may be moved distally with respect to the clip 102 until the loops 146 at the distal end 148 disengage the hinges 122. Once the loops 146 have been released from, for example, the C-shaped hinges 122, the distal ends 148 are permitted to revert to their biased configuration, moving radially away from one another. Thus, extending members 110, and the endoscope 104, may be withdrawn from the body so that just the clip 102 remains clipped over the target tissue.

As shown in FIGS. 11-14, a clipping system 200 according to another exemplary embodiment is substantially similar to the clipping system 100 except as detailed below. The system 200 comprises a clip 202 configured to be mounted to a distal end 206 of an endoscopic shaft 242 of an endoscope 204 via an adapter 208 to be inserted into a target area within a body via, for example, a body lumen as described above. Similarly to the clipping system 100, the clip 202 is releasably coupled to a pair of extending members 210, which facilitate movement of the clip 202 relative to the endoscopic shaft 242 and the adapter 208 between an insertion configuration, an initial deployed configuration, a review configuration and a final deployed configuration.

In the insertion configuration, the clip 202 is mounted over a distal portion 234 of the adapter 208 so that jaws 218 of the clip 202 are maintained in the insertion configuration. The clip 202 may be moved from the insertion configuration to the initial deployed configuration by moving the clip 202 distally along and off the adapter 208 so that the jaws 218 are permitted to revert to spring closed under their bias to the initial deployed configuration, immediately distal of the adapter 208. The system 100 may then be moved to the review configuration by moving the endoscopic shaft 224 proximally relative to the clip 202 as the extending members 210 play out so that the distal end 206 of the endoscopic shaft 224 is separated from the clip 202 via a distance selected so that the clip 202 is viewable via the endoscope 204 while the clip 202 remains coupled to the system 200 via the extending members 210.

In this embodiment, each of the extending members 210 is connected to one of the jaws 218 of the clip 202 rather than to the hinges 222 that connect the jaws 218 to one another. Thus, movement of the clip 202 to the final deployed configuration is achieved via a different mechanism than that described in regard to the clip 102.

In this exemplary embodiment, the clip 202 is substantially similar to the clip 102, including jaws 218 connected to one another via hinges 222 so that the clip 202 is movable between the insertion configuration, in which the jaws 218 are separated from one another to receive tissue therebetween and an initial deployed configuration, in which the jaws 218 are moved toward one another to grip the tissue received therebetween. Each of the jaws 218 in this embodiment extends along a curve from a first end 225 to a second end 227 where the first ends 225 of each of the jaws 218 are connected to one another via one of the hinges 222 and the second ends 227 are connected to one another via a second one of the hinges 222. Each of the jaws 218, in this embodiment, further includes an opening 276 extending therethrough sized and shaped to receive a portion of a corresponding one of the extending members 210 to form a releasable connection between each of the jaws 218 and its corresponding extending member 210. According to one example, the opening 276 is formed midway between the first end 225 and the second end 227 of each of the jaws 218. It will be understood by those of skill in the art, however, that the opening 276 be formed at any location on each of the jaws 218 so long as the opening 276 is configured to receive a corresponding one of the extending members 210 therein.

Each of the extending members 210 extends from a distal end 248, releasably coupled to the clip 202 via openings 276, to a proximal end 256. Rather than including a loop at the distal end 248, however, each of the extending members 210 is configured as, for example, a filament, strand or coil of metal or polymer, which includes an enlarged member 246 (e.g., enlarged ball) coupled to the distal end 248 via a separable connection. The distal end 248 of each of the extending members 210 is inserted through a corresponding one of the openings 276. The enlarged member 246 is then connected to the distal end 248 to prevent the extending members 210 from inadvertently separating from the clip 202 during movement of the clip 202 between the insertion configuration, the initial deployed configuration and the review configuration.

The clip 202, however, may be moved from the review configuration, in which the clip 202 is clipped over tissue, toward the final deployed configuration by drawing the extending members 210 proximally relative to the adapter 208 until the enlarged members 246 are pressed proximally against the jaws 218. When a force exerted thereon exceeds a predetermined threshold force, the enlarged members 246 will separate, break away or otherwise disconnect from the distal ends 248, so that the extending members 210 and the endoscope 204 are fully separated from the clip 202 and may be removed from the body while leaving the clip 202 in place clipped over target tissue.

Similarly to the extending members 110, distal portions 260 of the extending members 210 extend alongside an exterior surface 236 of a distal portion 234 of the adapter 208 while proximal portions 262 of the extending members 210 extend longitudinally through channels 266 extending through a wall 258 of the proximal portion 232. In one embodiment, the distal portions 260 of the extending members 210 extend along diametrically opposing sides of the distal portion 234. It will be understood by those of skill in the art, however, that the distal portions 260 may extend along any portion of the distal portion 234.

In this embodiment, the adapter may include two channels 266 configured to accommodate proximal portions 260 of the extending members 210. The channels 266 converge at a point at which proximal ends 256 of the extending members 210 meet and are connected to one another. As described above with respect to the clipping system 100, a control element (not shown) extends proximally from the proximal ends 256 of the extending members 210 to, for example, an actuating assembly substantially similar to the actuating assembly 112, so that movement of the extending members 210, and thereby the clip 202, may be controlled via movement of the control element relative to the endoscopic shaft 242. Similarly to the clipping system 100, the control element may extend through a coil 250 extending between a proximal end 226 of the adapter 208 and the actuating assembly, as described above with respect to the system 100.

It will be understood by those of skill in the art that the clipping system 200 may be utilized in a manner substantially similar to the clipping system 100. In particular, the clip 202 may be moved between the insertion configuration, the initial deployed configuration and the review configuration in a manner substantially similar to the clip 102. When it is desired to move the clip 202 to the final deployed configuration, however, the extending members 210 are drawn proximally relative to the clip 202 until tension on the extending members 210 generates a force exceeding the predetermined threshold force at which the enlarged members 246 are released from the distal ends 248 of the extending members 210. Once the enlarged members 246 have been separated from the distal ends 248, the extending members 210 may be removed from the openings 278 so that the extending members 210 and the endoscope 204 may be removed from the body while leaving the clip 202 in place clipped over the target tissue.

Figure 15:
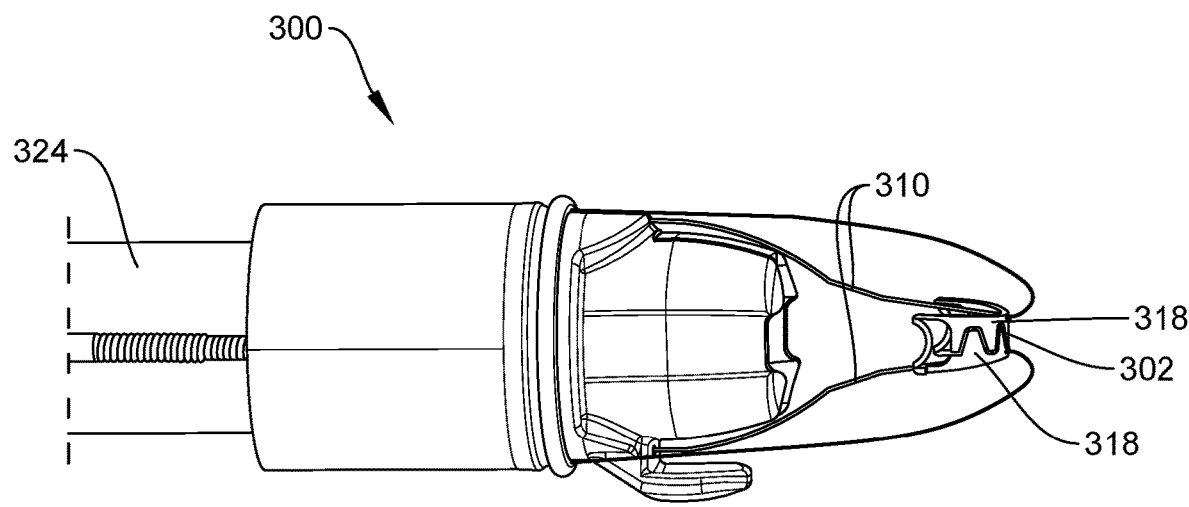
FIG. 15 shows a longitudinal side view of a distal portion of a system according to another exemplary embodiment of the present disclosure.
Figure 16:
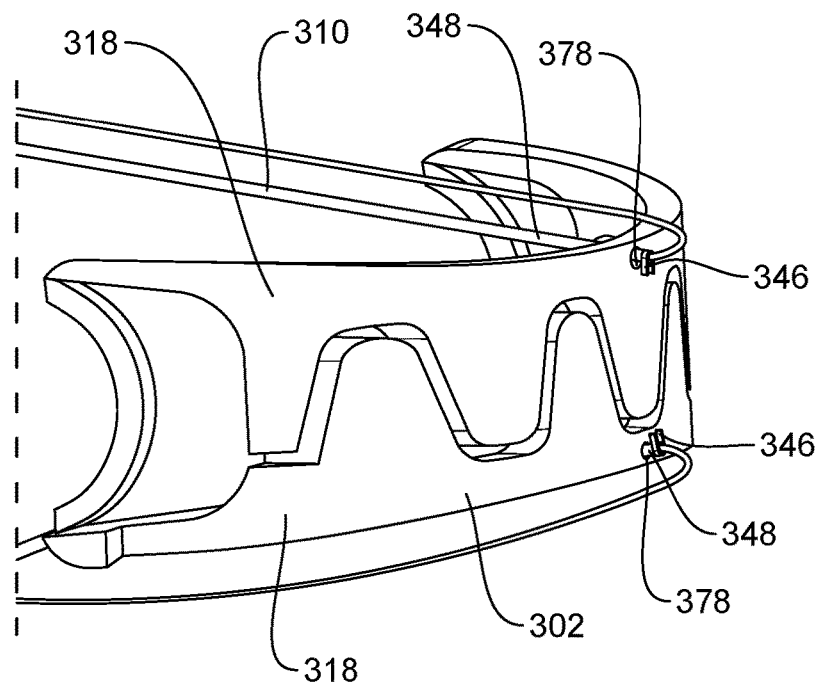
FIG. 16 shows an enlarged perspective view of the distal portion of the system of FIG. 15.

As shown in FIGS. 15-16, a clipping system 300 according to another exemplary embodiment of the present disclosure may be substantially similar to the clipping system 200 described above except for the distinctions detailed below. The clipping system 300 may also be utilized in a manner substantially similar to that described for the clipping systems 100 and 200 so that the clip 302 is movable between the insertion configuration, the initial deployed configuration and the review configuration via extending members 310 releasably coupled to the clip 302 via enlarged members 346 at distal ends 348 of the extending members 310, substantially as described above. Rather than being moved to a final deployed configuration via the exertion of a tension to the extending members 310 exceeding a predetermined threshold force, however, the clipping system 300 further includes a string 380 connected to the enlarged members 346 for disengaging the enlarged members 346 from the distal ends 348 of the extending members 310.

Similarly, to the extending members 210 and the clip 202 of the clipping system 200, distal ends 348 of the extending members 310 each include an enlarged member 346 releasably coupled to a corresponding one of the distal ends 348 so that, when it is desired to move a clip 302 to a final deployed configuration, each of the enlarged members 346 is disengaged from the corresponding distal end 348 to permit the extending members 310 to be removed from openings 378 extending through jaws 318 of the clip 302. Each string 380 extends from a distal end 381 connected to a corresponding one of the enlarged members 346 to, for example, an actuating assembly at a proximal end of an endoscopic shaft 324, as described above. Thus, when it is desired to move the clip 302 to the final deployed configuration, a user exerts a proximal force on the string 380 relative to the clip 302, which separates the enlarged member 346 from the distal end 348 of the extending member 310. Once the enlarged members 346 are no longer coupled to the distal ends 348, the extending members 310 may be drawn proximally out of the openings 378 so that the clip 302 is released from the extending members 310 in the final deployed configuration.

In one embodiment, the enlarged members 346 is a substantially U-shaped element fit over one of the distal ends 348 and held in place (via, e.g., a friction fit) until it is desired to be disengaged therefrom. It will be understood by those of skill in the art, however, that the enlarged members 346 may be formed in any of a variety shapes and configurations so long as the enlarged members 346 may be fit over the distal ends 346 so that they are releasable via the string 380. It will also be understood by those of skill in the art that the enlarged members 346 may be releasably coupled to the distal ends 348 via friction fit, adhesive, or other coupling mechanism, so long as the enlarged members 346 are releasable therefrom via the string 380.

Although the clipping system 300 is described and shown as including the string 380, it will be understood by those of skill in the art that the clipping system 300 may include any of a variety of removal elements extending from the enlarged member 346 to the actuating assembly. Removal elements may include, for example, any thread, filament or strand that is configured to pull the enlarged members 346 off of the distal ends 348 of the extending members 310.

Figure 17:
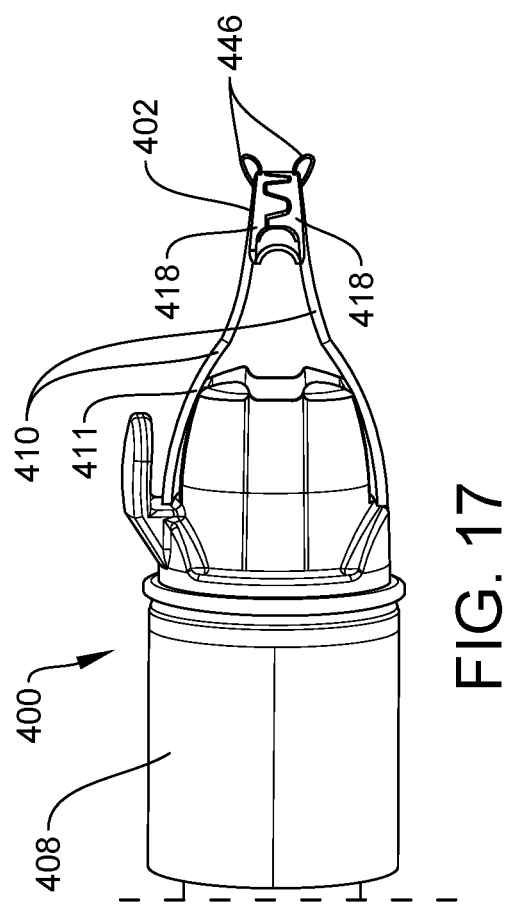
FIG. 17 shows a longitudinal side view of a distal portion of a system according to yet another exemplary embodiment of the present disclosure.
Figure 18:
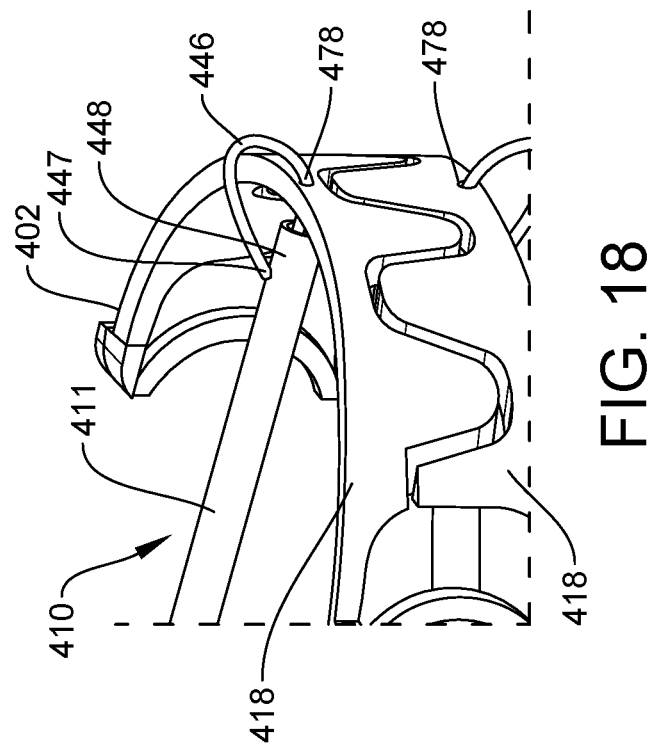
FIG. 18 shows an enlarged perspective view of the distal portion of the system of FIG. 17.
Figure 19:
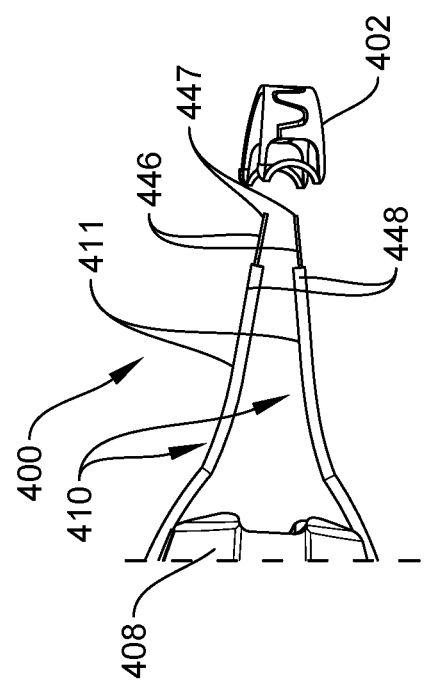
FIG. 19 shows a longitudinal side view of the distal portion of the system of FIG. 17, in a final deployed configuration.
Figure 23:
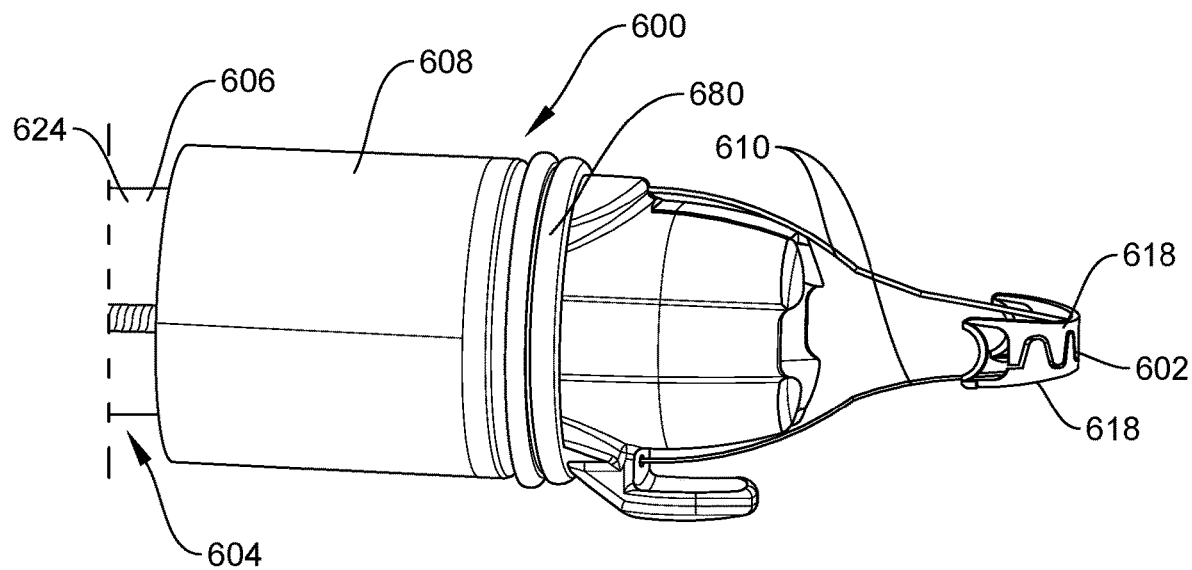
FIG. 23 shows a longitudinal side view of a distal portion of a system according to yet another exemplary embodiment of the present disclosure.
Figure 24:
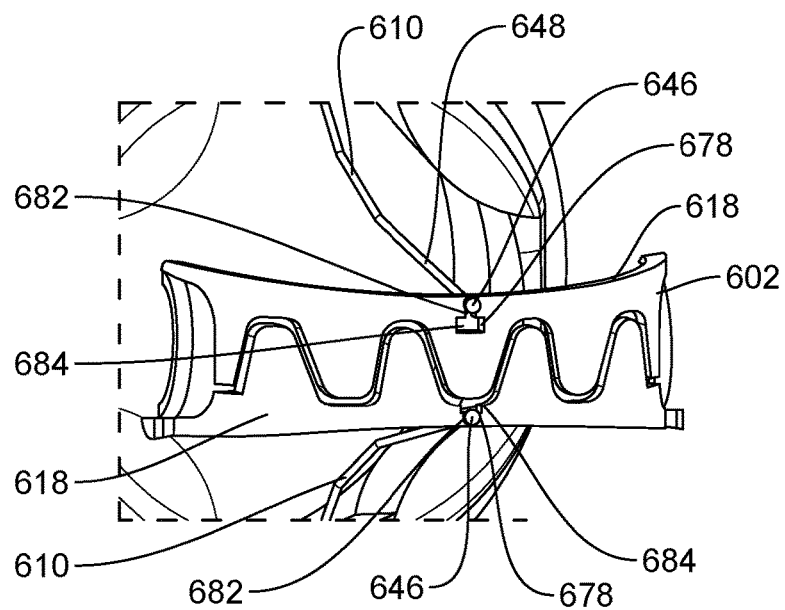
FIG. 24 shows an enlarged perspective view of the distal portion of the system of FIG. 23.
Figure 25:
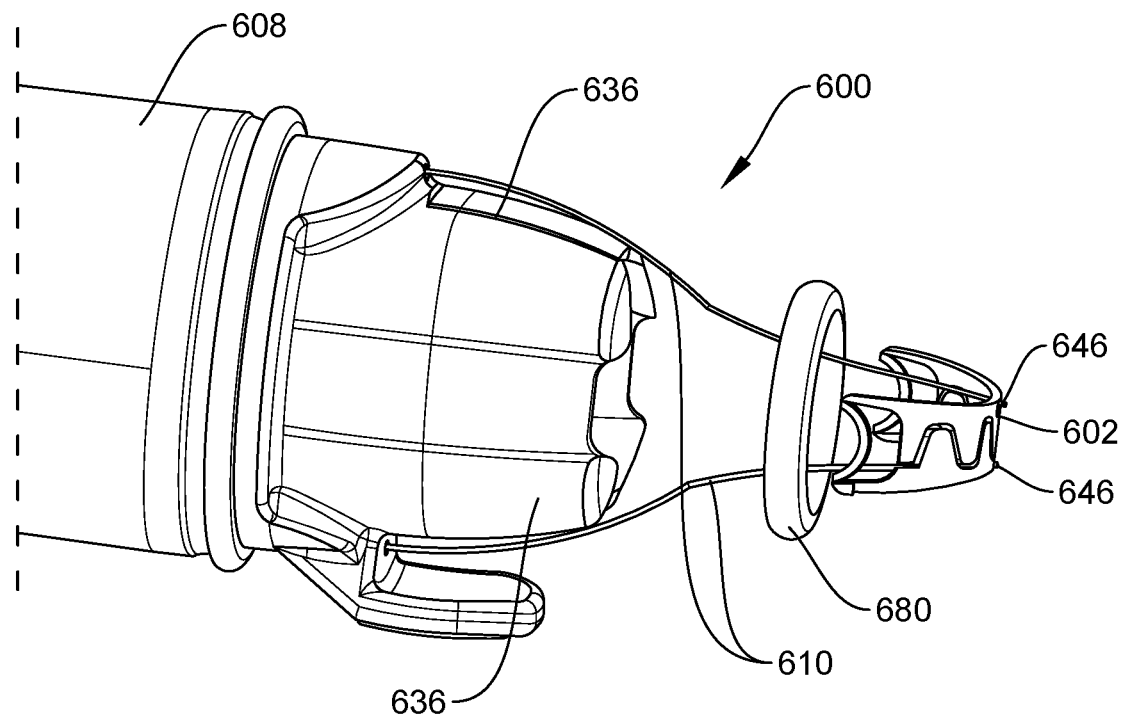
FIG. 25 shows a longitudinal side view of a distal portion according to another exemplary embodiment of the present disclosure.
Figure 26:
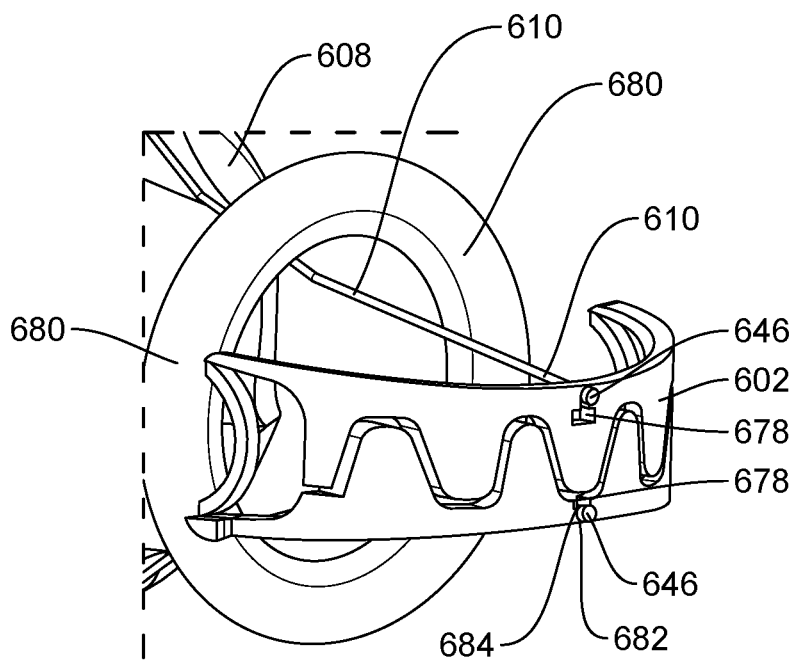
FIG. 26 shows an enlarged perspective view of the distal portion of the system of FIG. 25.

As shown in FIGS. 17-19, a clipping system 400 according to another exemplary embodiment may be substantially similar to any of the clipping systems 100, 200, 300, described above and differs therefrom only as described below. The clipping system 400 similarly comprises a clip 402 mountable to an endoscope via an adapter 408, the clip 402 is movable between an insertion configuration, an initial deployed configuration, a review configuration and a final deployed configuration via extending members 410. The clipping system 400 is substantially similar to the clipping system 200, except as described below.

The extending members 410, in this embodiment, includes coils 411 extending from proximal ends to distal ends 448. The coils 411 extend from proximal ends connected to one another to a control element extending proximally therefrom to control movement of the extending members 410, substantially as described above with respect to the clipping systems 100-300. Each of the extending members 410, however, further comprises a wire 446 extending distally from the distal end 448, the wire 446 configured to be looped through an opening 478 extending through a corresponding jaw 418 of the clip 402. In particular, the wire 446 may be looped through the opening 478 and a distal end 447 of the wire 446 attached to the distal end 448 of the coil 411 so that the extending member 410 is coupled to the clip 402 via the loop formed via the wire 446.

The distal end 447 of the wire 446 may be attached to the distal end 448 of the coil 448 via, for example, welding, crimping or gluing. This attachment is configured so that, when it is desired to disengage the extending members 410 from the clip 402 to move the clip 402 toward the final deployed configuration, the user exerts a proximal force along the extending members 410 relative to the clip 402 (which is clipped over target tissue) until the attachment is broken so that the wire 446 may be removed from the opening 478. It will be understood by those of skill in the art that the attachment is broken when the force exerted therein exceeds a predetermined threshold value. Once the attachment is broken, the extending members 410 and the endoscope may be removed from a body so that just the clip 402, which is clipped over a target tissue, as desired, remains.

As shown in FIGS. 20-21, a clipping system 500 according to yet another exemplary embodiment is substantially similar to the clipping systems 200-400 described above, comprising a clip 502 mountable to a distal end 506 of an endoscope 504 and movable between an insertion configuration, an initial deployed configuration, a review configuration and a final deployed configuration via extending members 510 releasably coupled to the clip 502. The clipping system 500 may be substantially similar to the clipping systems described above, except as detailed below. Proximal portions 562 and distal portions 560 of the extending members 510, in this embodiment, are coupled to one another via a releasable coupling 564 configured to separate, break or otherwise release to allow the clip 502 to be moved toward the final deployed configuration.

Each of the proximal and distal portions 562, 560 of the extending members 510 is comprised of separate strands of, for example, string, which are releasably coupled to one another via the releasable coupling 564. Similarly to the extending members described above with respect to the clipping systems 100-400, proximal ends of the proximal portions 562 may be connected to one another and to a control element 558 for controlling a movement of the extending members 510 relative to the endoscope 504. According to one exemplary embodiment, the releasable coupling 564 includes a holding element 586. The holding element 586 in this embodiment is C and/or bracket shaped so that an interior space 590 of the holding element 586 is open to an exterior thereof along one side. The holding element 586 extends from a proximal end 587 fixedly attached to a distal end 563 of the proximal portion 562 and a distal end 588 including a U-shaped slot 589 via which the distal portion 560 is releasably coupled to the holding element 586. The interior 590 extends between the proximal and distal ends 587, 588 so that the U-shaped slot 589 is in communication with both the interior space 590 and with the exterior of the holding element 586.

Each of the distal portions 560 of the extending members 510 extends from an enlarged proximal end 559 to a distal end 561 non-releasably coupled to the clip 502 via an opening 578 extending through a corresponding jaw 518 of the clip 502. The distal end 561 may, for example, be non-releasably connected to the jaw 518 via a ball. It will be understood by those of skill in the art that this ball is sized so that the ball cannot pass through the opening 578. In a coupled configuration, the enlarged proximal end 559 may be received within the interior 590 of the holding element 586 so that a portion of the distal portion 560 of the extending member 510 distal of the proximal end 559 extends through the distal end 588 of the holding element 586 via the slot 589. Similarly to the distal end 561, the enlarged proximal end 559 may be configured as a ball sized so to have a diameter larger than a width of the slot 589, so that the enlarged proximal end 559 cannot pass longitudinally through the slot 589.

The holding element 586 of each releasable coupling 564 is slidably housed within a channel 566 extending through a proximal portion 532 of the adapter 508, when the clip 502 is in the open insertion configuration, the initial deployed configuration and the review configuration. When in the open insertion configuration, the initial deployed configuration and the review configuration the enlarged proximal end 559 of the distal portion 560 is maintained within the interior space 590 of the holding element 586 via the proximal and distal ends 587, 588 of the holding element 586 and via an interior surface of the channel 566.

When it is desired to move the clip 502 toward the final deployed configuration, however, the extending members 510 are moved even further distally relative to the adapter 508 until the holding element 586 is moved distally past a distal end of the channel 566 so that the enlarged proximal end 559 is released from the interior of the channel 566 and is no longer held in the interior space 590 via the channel 560. Once the enlarged proximal end 559 has been released from the holding element 586, the proximal portions 562 of the extending members 510 and the endoscope 504 may be removed, leaving the clip 502, with the distal portions 560 attached thereto, remaining in the body clipped over a target tissue, as desired.

Although the distal portion 560 of the extending member 510 is described and shown as non-releasably coupled to the jaws 518 of the clip 502 via a ball, it will be understood by those of skill in the art that the distal portion 560 may be non-releasably coupled to the clip 502 via any of a variety of coupling mechanisms. In one alternate embodiment, as shown in FIG. 22, a distal portion 560' of an extending member 510' may be configured as a strand looped through an opening 578' of a corresponding jaw 518' of a clip 502'. Similarly to the extending member 510, the distal portion 560' may have an enlarged proximal end 559' via which the distal portion 560' is releasably coupled to a holding element 586' of a releasable coupling 564' for coupling the distal portion 560' to a proximal portion 562' of an extending member 510'.

According to another exemplary embodiment, as shown in FIGS. 23-26, a clipping system 600 may be substantially similar to any of the clipping systems described above. The clipping system 600 comprises a clip 602 configured to be mountable over a distal end 606 of an endoscopic shaft 624 via an adapter 608. The clip 602 is movable relative to the adapter 608 and the endoscopic shaft 624 via extending members 610, which facilitate movement of the clip 602 between an insertion configuration, an initial deployed configuration, a review configuration and a final deployed configuration. Similarly to the clipping system 200, each of a pair of extending members 610 is connected to a corresponding jaw 610 of the clip 602. The clipping system 600, however, further comprises an elastic band 680 for disengaging the extending members 610 from the clip 602 to move the clip 602 toward the final deployed configuration, as will be described in further detail below.

Similarly to the extending members 210, the extending members 610 extend from proximal ends 656 to distal ends 648. The proximal ends 656 are connected to one another and a control element, which extends proximally therefrom. The distal ends 648 each include an enlarged member 646 thereon. The enlarged member 646, however, is fixed thereon and cannot be removed from the distal end 648. The distal ends 648, in this embodiment, are biased toward a radially outward position. In other words, the distal ends 648 are biased away from one another so that each of the distal ends 648 extend radially away from a longitudinal axis of the adapter 608.

Similarly to the clip 202, each of the jaws 618 includes an opening 678 extending therethrough for receiving a portion of a corresponding one of the extending members 610 releasably therein. Each of the openings 678, however, includes a first portion 682 sized and shaped to prevents the enlarged member 246 to be passed therethrough and a second portion 684 sized and shaped to permit the enlarged member 246 to pass. The openings 678 are configured so that the first portions 682 are in a radially outward position relative to the second portions 682. Thus, in a coupled configuration, a portion of the extending members 610 immediately proximal of the enlarged members 646 are received within the first portions 682 while the enlarged members 646 abut against the jaws 118 and are prevented from passing therethrough.

The clip 602 may be moved between the insertion configuration, the initial deployed configuration and the review configuration to grip a target tissue, in a manner substantially similarly to that described in regard to the clipping systems described above. In the insertion configuration, the initial deployed configuration and the review configuration the elastic band 680 extends about a portion of the adapter 608. Upon confirmation that the target tissue has been gripped by the clip 602, as desired, the elastic band 680 is moved distally off the adapter 608 so that the elastic band 680 extends about the extending members 610, distally of the adapter 608, drawing the extending members 610 toward one another so that the distal ends 648 are moved toward one another and the enlarged members 646 thereof are permitted to pass through the second portions 684 of the openings 678. Thus, the extending members 610 and the endoscope 604 are removable from the body while the clip 602 remains gripped over the target tissue.

It will be understood by those of skill in the art that the elastic band 680 may be deployed from the adapter 608 via any of a variety of mechanisms so long as the elastic band 680 is movable distally over the extending members 610 to move the extending members 610 from the first portions 682 of the openings 678 to the second portions 684. In one example, a distal portion of a thread or other strand may be wound around a portion of the elastic band so that when a proximal end of this strand is drawn proximally by a user, the distal portion of the strand begins to unwind, causing the elastic band 680 to roll distally off of a tapered exterior surface 636 along a distal portion 634 of the adapter 608.

Although the exemplary embodiments show and describe the elastic band 680 for moving the extending members 610 to facilitate the final deployment of the clip 602. It will be understood by those of skill in the art that any of a variety of mechanisms maybe utilized for moving the clip 602 to the final deployment so long as the extending members 610 may be restricted toward one another so that the enlarged members 646 at the distal ends 648 are passable through the second portions 684 of the openings 678. In another embodiment, for example, a snare may be deployed about the extending members 610, distally of the adapter 608, to draw the extending members 610 toward one another so that the distal ends 648 are moved into the second portions of the openings 678 and thereby removable from the clip 602.

Figure 27:
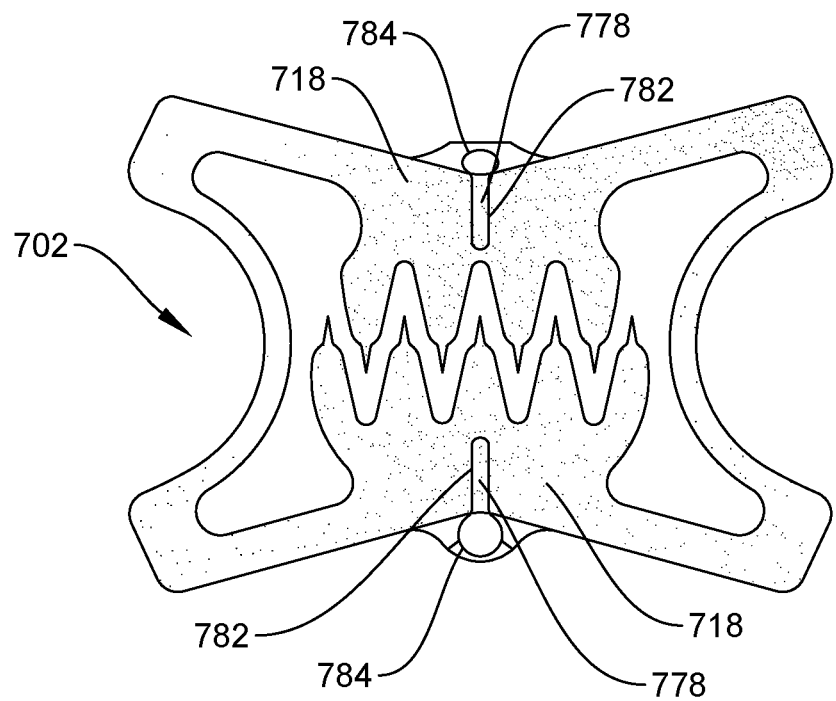
FIG. 27 shows a plan view of a clip according to a system according to another exemplary embodiment of the present disclosure.
Figure 28:
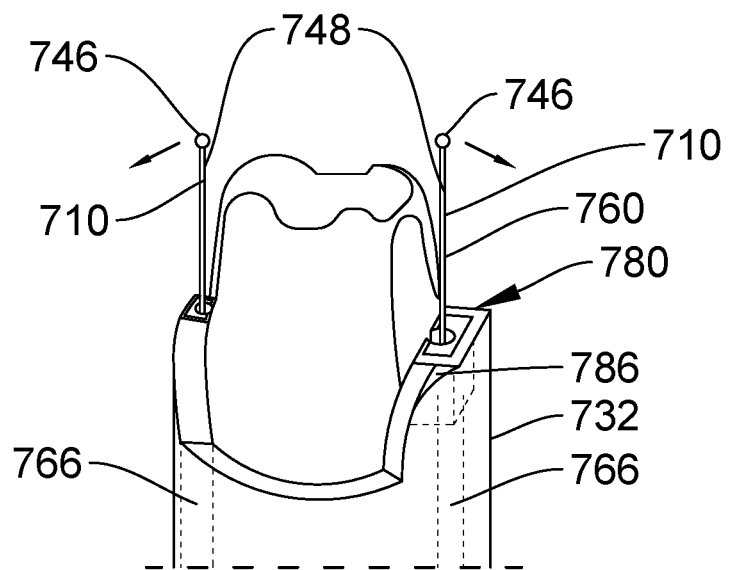
FIG. 28 shows a perspective view of an adapter and extending members according to the system of FIG. 27.
Figure 29:
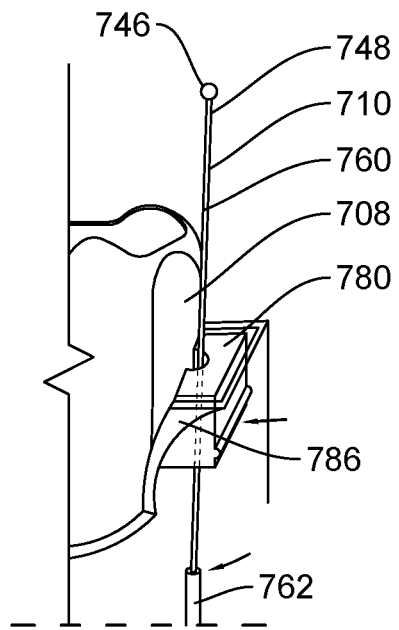
FIG. 29 shows a partial enlarged perspective view of the adapter and extending members of FIG. 28.

As shown in FIGS. 27-29, a clipping system according to yet another exemplary embodiment may be substantially similar to the clipping system described above, comprising clip 702, as shown in FIG. 27, configured to be mounted to a distal end of an endoscope via an adapter 708, as shown in FIGS. 28-29. Similarly to the previously described clipping systems, the clip 702 is movable relative to the adapter 708 and the endoscope between an insertion configuration, an initial deployed configuration, a review configuration and a deployed configuration via extending members 710 releasably coupled to jaws 718 of the clip 702.

As will be described in further detail below, however, the extending members 710 according to this embodiment are keyed to a portion of the adapter 708, so that as the extending members 710 are moved distally with respect to the adapter, distal portions 760 of the extending members 710 are forced to extend radially outwardly to disengage the clip 702 from the extending members 710 in the final deployed configuration. It will be understood by those of skill in the art that the clipping system 700 may be substantially similar to the clipping systems described above, except as detailed below.

Similarly to the clip 602, the clip 702, as shown in FIG. 27, is comprised of jaws 718, each jaw 718 including an opening 778 defined via first and second portions 782, 784 extending therethrough for releasably engaging a corresponding one of the extending members 710. In this embodiment, however, the first portion 782 is positioned radially inwardly of the second portion 784 and is sized and shaped to have a smaller width than an enlarged end 746 at a distal end 748 of the extending member 710. The second portion 784 is sized, shaped and configured to permit the enlarged end 746 to be passed therethrough.

The extending members 710 extend from proximal ends to distal ends 748 including the enlarged member 746. The proximal ends, as described with respect to the clipping systems 100-600, may be connected to one another and to a control element which extends proximally therefrom to an actuating assembly for moving the clip 702 between the insertion, initial deployed, viewing, and final deployed configurations. A distal portion 760 of each of the extending members 710 may taper toward the distal end 748. A proximal portion 762 of the extending members 710 has a larger diameter than the distal portion 760.

Similarly to the clipping systems described above, proximal portions 762 of the extending members 710 are slidably received within corresponding channels 766 extending through proximal portions 732 of the adapter 708. In this embodiment, however, the adapter 708 includes a key feature 780 movably received within the adapter 708 at a distal end of each of the channels 766. In the insertion, initial deployed and the review configuration, the key feature 780 is in a first position relative to the channel 766 of the adapter 708. Th key feature 780 is maintained in this first portion via a friction fit with a portion of the channel 760. In the final deployed configuration, the key feature 780 is moved to a second position in which the key feature is moved radially outwardly with respect to a longitudinal axis of the adapter 708. As will be described in greater detail below, the larger diameter of the proximal portion 762 of the extending member 710 pushes the key feature toward this second position.

In the insertion, initial deployed and the review configuration, the distal portion 760 of the extending member 710 is moved slidably along the key feature 780, with the distal end 748 of the extending member 710 releasably coupled to the opening 778 via the first portion 782 of the opening 778. When it is desired to release the clip 702 from the extending members 710 in the final deployed configuration, however, the adapter 708 is moved proximally with respect to the extending members 710 until the larger diameter of the proximal portion 762 engages the ramped surface 786 to move the key feature 780 from the first position toward the second position. The extending member 710, which is pushed against the ramped surface, also moves radially outwardly to move the distal end 748 from within the first portion 782 of the opening 748 to the second portion 784 of the opening 778. Thus, the enlarged end 746 is permitted to pass through the opening 778 so that the extending member 710 may be removed therefrom, leaving just the clip 702 clipped over a target tissue.

Although the exemplary embodiment specifically describes movement of the distal portion 760 in a radially outward direction to release the enlarged end 746 from the opening 778 and leave the clip 702 in the final deployed configuration, it will be understood by those of skill in the art that the clipping system 700 may be modified so that the distal portions 760 of the extending members 110 are required to move in a radially inward direction relative to the longitudinal axis of the adapter 708 to be released from the opening 778. In particular, in another embodiment, when the larger diameter of the proximal portion 762 engages the ramped surface 786 of the key feature 780, the key feature 780 is moved radially inward and the distal portion 760, which is pressed thereagainst, is also moved in a radially inward direction. It will be understood by those of skill in the art that the first and second portions 782, 784 of the openings 787 will be correspondingly configured.

Figure 30:
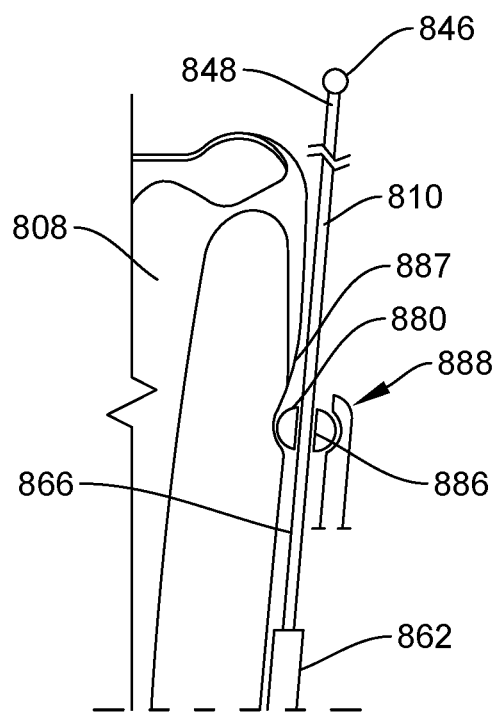
FIG. 30 shows a partial enlarged perspective view of an adapter and extending members according to another exemplary embodiment of the present disclosure.

FIG. 30 shows another exemplary embodiment of an adapter 808 and extending members 810, which may be used in combination with the clip 702 of the clipping system described above. The extending members 810 may be substantially similar to the extending members 710, described above. Rather than a key feature including a ramped surface at distal ends of channels 866 extending through a proximal portion 832 of the adapter 808, however, each of the channels 866 of the adapter 808 includes a key feature configured as a sphere 880 with a channel 886 extending therethrough for slidably receiving a distal portion 860 of one of the extending members 810 therein.

The sphere 888 is received within a socket 888 formed at the distal end of a corresponding one of the channels 866 so that the sphere 888 is rotatable between a first position, in which a longitudinal axis of the channel 886 of the sphere 880 is substantially coaxially aligned with a longitudinal axis of the channel 866, and a second position in which the longitudinal axis of the channel 886 of the sphere 880 is angled with respect to the longitudinal axis of the channel 866 of the adapter 808. A portion of the socket 88 includes a ramped surface 887 extending therealong so that, when the sphere 880 is moved distally thereagainst, the sphere 880 rotates from the first position to the second position.

In the insertion, initial deployed and the review configurations, the sphere 880 is in the first position relative to the adapter 808 so that the distal portion 860 of the extending member 810 is slidably received through the channel 886 of the sphere 880 and a distal end 848 of the extending member 810 is releasably coupled to the opening 778 of the clip 702 via the first portion 782 of the opening 778. When it is desired to release the clip 702 from the extending members 810 in the final deployed configuration, however, the adapter 808 is moved proximally relative to the extending members 810 until a larger diameter of a proximal portion 862 of the extending member 810 engages a portion of the sphere 880, pushing the sphere 880 distally against the ramped surface 887 of the socket 888 to move the sphere 880 from the first position to the second position. Thus, the distal portion 860 of the extending element 810 is angled with respect to the proximal portion 862 of the extending members 810 so that the distal portion 860 is moved radially outward relative to a longitudinal axis of the adapter 808. When the sphere 880 is moved toward the second position, the distal end 848 is moved into the second portion 884 of the opening 878 so that the enlarged end 846 may pass through the second portion 884 to release the clip 702 from the extending member 810.

Although the exemplary embodiment specifically describes movement of the distal portions 860 of the extending members 810 radially outward to release the enlarged end 846 from the opening 878 leaving the clip 702 in the final deployed configuration, it will be understood by those of skill in the art that the clipping system may be modified so that the distal portions 860 of the extending members 810 move radially inward relative to the longitudinal axis of the adapter 808 via a rotation of the sphere 880 in an opposite direction than as described above. It will be understood by those of skill in the art that first and second portions 782, 784 of the opening 778 in this embodiment, will be correspondingly configured to facilitate a release of the extending members 810 therefrom when the distal portions 860 are moved in a radially inward direction relative to the longitudinal axis of the adapter 808.

Figure 31:
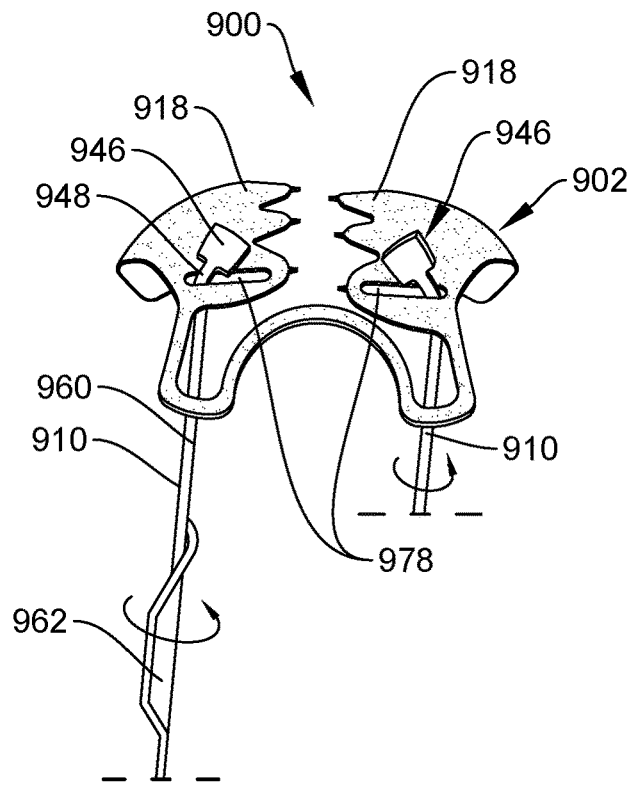
FIG. 31 shows a perspective view of a system according to yet another exemplary embodiment of the present disclosure.
Figure 32:
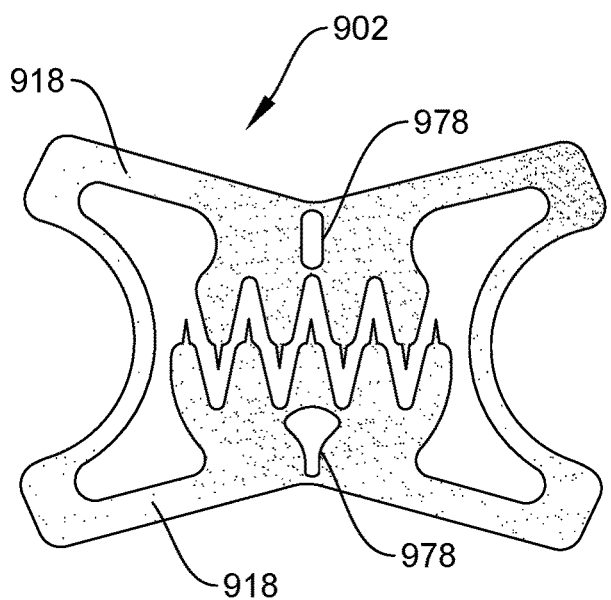
FIG. 32 shows a plan view of a clip according to the system of FIG. 31.

As shown in FIGS. 31-32, a clipping system according to yet another exemplary embodiment may be substantially similar to the clipping systems described above, comprising a clip 902 configured to be mountable over a distal end of an endoscope via an adapter 908 which is mounted to the distal end of the endoscope. The clip 902 movable relative to the adapter 808 between an insertion configuration, an initial deployed configuration, a review configuration, and a final deployed configuration via extending members 910 releasably coupled to the clip 902.

As discussed above with respect to the systems 100-800, the clip 902 is moved between the insertion configuration, the initial deployed configuration, and the review configuration by moving the extending members 910 longitudinally with respect to the adapter 908. The clip 902, however, is released from the extending members 910 to be moved toward the final deployed configuration via a rotation of the extending members 910, as will be described in further detail below. It will be understood by those of skill in the art that the clipping system 900 is substantially similar to the clipping systems described above, except as described below.

The clip 902 may be substantially similar to the clips 102-702, including a pair of jaws 918, each jaw 918 including an opening 978 extending therethrough for releasably engaging a distal end 948 of the extending members 910. In this embodiment, however, the openings 978 may be keyed to the enlarged members 946 at the distal end 948 of the extending members 910. For example, each of the opening 978 may be configured as a slotted opening sized and shaped to receive, for example, a flattened enlarged member 946 at the distal end 948 of the extending member 910. The slotted opening 978 is sized, shaped and configured so that, when the flattened enlarged member 946 is in an unlocked orientation relative to the slotted opening 978, the flattened enlarged member 946 may be passed therethrough. When the flattened enlarged member 946 is rotated relative to the opening 978 from the unlocked orientation about a longitudinal axis of the extending member 910 to a locked orientation different than the first orientation, the enlarged member 946 cannot pass through the slotted opening 978 so that a distal end 948 of the extending member 910 is releasably coupled thereto.

In one exemplary embodiment, an angle of rotation between the first and second positions of the flattened enlarged member 946 relative to the slotted opening 946 may be approximately 90 degrees. It will be understood by those of skill in the art that the rotation of the extending members 910 between the first and second orientations relative to the opening 978 may have any of a variety of angles so long as the enlarged member 946 is rotatable relative to the opening 978 between the locked and unlocked orientations.

In one embodiment, the flattened enlarged member 946 may be substantially symmetrically shaped and a size and shape of the slotted opening 978 may substantially correspond to the shape of the flattened enlarged member 946. It will be understood by those of skill in the art, however, that the opening 978 and the flattened enlarged member 946 may have any of a variety of shapes and sizes so long as the slotted opening 978 and the enlarged member 946 are keyed to one another—e.g., a rotation of the flattened enlarged member 946 relative to the slotted opening 978 moves the extending members 910 and the clip 902 between the locked and unlocked orientations.

Similarly to the clipping devices described above, proximal portions 960 of the extending members 910 are received within channels extending through a proximal portion of the adapter 908, while distal portions 960 of the extending member 910 extend distally therefrom alongside an exterior surface of a distal portion if the adapter 908 to engage the clip 902. The clipping system 902 may be moved between the open insertion configuration, the initial deployed configuration and the viewing configuration via a longitudinal movement of the extending members 910 relative to the adapter 908, substantially as described above with respect to the previously described clipping systems. In the open insertion configuration, the initial deployed configuration and the review configuration, the enlarged members 946 is in the locked configuration relative to the openings 978.

When it is desired to move the clip 902 toward the final deployed configuration by releasing the clip 902 from the extending members 910, however, the adapter 908 is moved proximally with respect to the extending members 910 are moved further distally with respect to the adapter 908 until keyed features 980 extending along the proximal portions 960 of the extending members 910 engage a correspondingly keyed (e.g., threaded) portion of the channels of the adapter 908 to rotate relative to the channels and the openings 978 from the locked configuration to the unlocked configuration.

It will be apparent to those skilled in the art that various modifications may be made in the present disclosure, without departing from the scope of the disclosure.

What is claimed is:

1. A clipping system for treating tissue, comprising:
   an adapter extending longitudinally from a proximal end configured to be mounted over a distal end of an insertion device to a distal end, wherein a distal portion of the adapter is tapered toward the distal end of the adapter;
   a clip including first and second jaws, a first end of the first jaw being connected to a first end of the second jaw via a first hinge and a second end of the first jaw being connected to a second end of the second jaw via a second hinge so that the first and second jaws are movable between an insertion configuration, in which the clip is mounted over the adapter so that the first and second jaws are separated from one another to receive tissue therebetween, and an initial deployed configuration in which the first and second jaws are drawn toward one another to grip tissue therebetween, at least one of the first and second hinges being biased to draw the clip toward the initial deployed configuration; and
   a first extending member releasably coupled to the clip and movably connected to the adapter to permit a movement of the clip relative to the adapter from the insertion configuration to the initial deployed configuration, the first extending member being configured to permit withdrawal of the adapter proximally away from the clip while the first extending member remains coupled to the clip to place the system in a review configuration in which the clip is physically separated from the adapter to enhance a visual observation of the clip, the first extending member being operable to retract the clip proximally over the adapter so that the clip is forced open as the clip is retracted over the adapter freeing the clip from tissue on which it has been clipped, and the first extending member configured to release the clip therefrom in a final deployed configuration, when the clip is observed to be clipped in a desired position.

2. The system of claim 1, further comprising a second extending member releasably coupled to the clip and movably connected to the adapter, the second extending member being configured to remain coupled to the clip while the clip is moved toward the initial deployed configuration and while the system is moved to the review configuration, the second extending member being operable to cooperate with the first extending member to retract the clip proximally over the adapter from one of the review and initial deployment configurations, and to release the clip therefrom in the final deployed configuration.

3. The system of claim 2, wherein proximal ends of the first and second extending members are connected to one another and to a control element extending proximally therefrom to a proximal end accessible to a user of the system.

4. The system of claim 3, wherein distal ends of each of the first and second extending members include a loop configured to be hooked over a portion of a corresponding one of the first and second hinges, the distal ends of each of the first and second extending members are biased radially away from a longitudinal axis of the adapter so that, when loops of the first and second extending members are hooked over the first and second hinges, respectively, the distal ends of the first and second extending members are restrained toward an engaging configuration, and when the distal ends of the first and second extending members are disengaged from the first and second hinges, the distal ends of the first and second extending members spring laterally outward to release the clip therefrom in the final deployed configuration.

5. The system of claim 1, wherein the clip is mountable in the insertion configuration over the distal portion of the adapter, and wherein the tapering of the distal portion of the adapter is configured to reduce a tension along the first extending member causing the clip to slide distally along the distal portion of the adapter from the insertion configuration toward the initial deployed configuration.

6. The system of claim 5, wherein the distal portion of the adapter includes a flat portion along an exterior surface thereof for reducing a friction between the clip and the adapter when the clip is moved distally therealong from the insertion configuration toward the initial deployed configuration, and a projection extending radially inward from an interior surface of the distal portion of the adapter configured to engage a portion of the clip when the clip is moved from the initial deployed configuration toward the insertion configuration.

7. The system of claim 1, wherein the first jaw includes an opening extending therethrough for engaging the first extending member.

8. The system of claim 7, wherein the first extending member includes an enlarged member releasably connected to the distal end of the first extending member, the first extending member releasably coupled to the opening of the first jaw via the enlarged member.

9. The system of claim 8, wherein the clip is movable from the review configuration to the final deployed configuration by drawing the first extending member proximally relative to the adapter until the enlarged member is pressed proximally against the first jaw and a force exerted thereon exceeds a predetermined threshold value so that the enlarged member is disengaged from the distal end of the first extending member.

10. The system of claim 8, further comprising a strand connected to the enlarged member and extending proximally therefrom so that, the clip is movable from the review configuration to the final deployed configuration by pulling the strand proximally until the enlarged member is disengaged from the distal end of the first extending member.

11. The system of claim 7, wherein the first extending member includes a coil extending from a proximal end to a distal end, a wire extending from the distal end of the coil to be looped through the opening of the first jaw, a distal end of the wire releasably attached to the distal end of the coil so that the first jaw is releasably coupled to the clip via the wire.

12. The system of claim 7, wherein the first extending member includes a proximal portion and a distal portion connected to one another via a releasable connection, the distal portion connected to the clip via the opening extending through the first jaw.

13. The system of claim 12, wherein the releasable connection includes a holding element including a first end fixedly attached to the proximal portion of the first extending member and a second end releasably attached to the distal portion of the first extending member so that, when the holding element is moved distally past a distal end of a channel of the adapter, the distal portion of the first extending member is released therefrom.

14. A clipping system for treating tissue, comprising:
an endoscope including a shaft extending longitudinally from a proximal end to a distal end;
an adapter including a proximal portion mounted over the distal end of the shaft of the endoscope and a distal portion extending distally from the proximal portion, the distal portion tapered toward a distal end thereof;
a clip configured to be mounted over the distal portion of the adapter, the clip including first and second jaws, a first end of the first jaw being connected to a first end of the second jaw via a first hinge and a second end of the first jaw being connected to a second end of the second jaw via a second hinge so that the first and second jaws are movable between an insertion configuration, in which the first and second jaws are separated from one another to receive tissue therebetween, and an initial deployed configuration in which the first and second jaws are drawn toward one another to grip tissue therebetween, at least one of the first and second hinges being biased to draw the clip toward the initial deployed configuration;

first and second extending members releasably coupled to the clip at distal ends thereof and movably connected to the adapter so that a longitudinal movement of the first and second extending members relative to the adapter moves the clip between the insertion configuration, the initial deployed configuration, in which the clip is moved toward a closed configuration immediately distal of the adapter, a review configuration, in which the clip is separated from a distal end of the endoscope via a distance selected so that the clip is visible via the endoscope, and a final deployed configuration, in which the clip is released from the extending member in the closed configuration; and a control element connected to proximal ends of the first and second extending members to extend proximally therefrom.

15. The system of claim 14, further comprising:

a coil extending proximally from the adapter and configured to slidably receive the control element therein; and an actuating assembly including a handle member and a spool mounted thereover and longitudinally movable relative thereto, the handle member connected to a proximal end of the coil and the spool connected to a proximal end of the control element so that the spool is moved relative to the handle member to move the clip between the insertion configuration, the initial deployed configuration, the review configuration and the final deployed configuration.

* * * * *